United States Patent [19]

Töpfl

[11] Patent Number: 4,921,955
[45] Date of Patent: May 1, 1990

[54] PROCESS FOR THE SYNTHESIS OF 1-SUBSTITUTED IMIDAZOLE-5-CARBOXYLIC ACIDS AND CARBOXYLIC ACID DERIVATIVES

[75] Inventor: Werner Töpfl, Dornach, Switzerland

[73] Assignee: Ciba-Geigy Corporation, Ardsley, N.Y.

[21] Appl. No.: 136,167

[22] Filed: Dec. 18, 1987

[30] Foreign Application Priority Data

Nov. 6, 1987 [CH] Switzerland .................. 4331/87

[51] Int. Cl.$^5$ ............... C07D 413/00; C07D 211/40; C07D 401/00; C07D 417/00; C07D 417/02; C07D 417/04; C07D 403/00; C07D 213/00
[52] U.S. Cl. ..................... 544/60; 546/210; 546/216; 546/225; 546/226; 546/229; 546/232; 546/233; 546/235; 546/269; 546/272; 546/273; 546/274; 546/278; 546/5; 546/141; 546/142; 546/143; 546/144; 546/153; 546/155; 546/156; 546/157; 546/158; 546/159; 546/165; 546/193; 546/194; 546/195; 546/196; 546/208; 546/209; 546/200; 546/201; 546/202; 546/15; 546/16; 546/17; 546/18; 548/336; 548/341; 548/342; 548/343; 548/104; 558/391; 558/430; 558/445; 558/452; 544/4; 544/139; 544/295; 544/230; 544/370; 540/541; 540/543; 540/603
[58] Field of Search ............ 544/139, 295, 370, 60, 544/230, 4; 546/15, 16, 17, 18, 141, 142, 143, 144, 153, 155, 156, 157, 158, 159, 165, 193, 194, 195, 196, 208, 209, 210, 200, 201, 216, 202, 225, 226, 229, 232, 233, 235, 269, 272, 273, 274, 278, 5; 548/336, 341, 104, 342, 343; 540/541, 543, 603

[56] References Cited

U.S. PATENT DOCUMENTS 4,182,624  1/1980  Söder et al. ..................... 71/92
4,761,483  8/1988  Lawson et al. .................. 548/342

FOREIGN PATENT DOCUMENTS 000373  7/1978  European Pat. Off. ............ 544/139
137868  10/1983 European Pat. Off. ............ 544/139
199206  4/1986  European Pat. Off. ............ 544/139
207563  6/1986  European Pat. Off. ............ 544/139
234656  2/1987  European Pat. Off. ............ 544/139
240050  3/1987  European Pat. Off. ............ 544/139

OTHER PUBLICATIONS

J. Am. Chem. Soc., vol. 71, 644–647, (1949), 2444–2448.

Organic Chem. The Name Game, pp. 258, 259 & 264, (1987).

Primary Examiner—Mary C. Lee
Assistant Examiner—J. Richter
Attorney, Agent, or Firm—Kevin T. Mansfield

[57] ABSTRACT

The invention relates to a process for the preparation of 1,5-disubstituted imidazoles of the formula

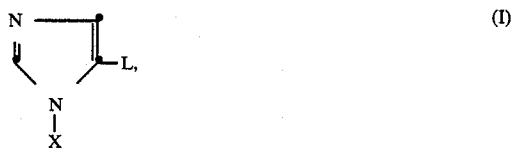

by alkylation of an N-cyanoformamidine of the formula II

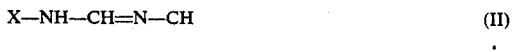

to form an N,N-disubstituted N′-cyanoformamidine of the formula

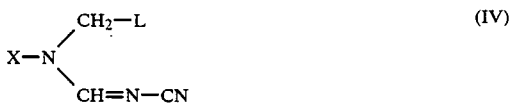

which is cyclised under the action of bases to form a 4-aminoimidazole of the formula

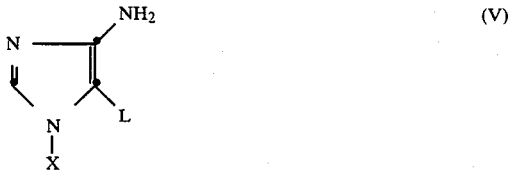

and then reduced to form the product of the formula I.

The invention relates also to a special process for the reduction of the aminoimidazole V to I, and to intermediate compounds for carrying out this process and to processes for the preparation of the intermediate compounds.

The meaning of the substituents X and L is explained in detail in the text.

3 Claims, No Drawings

PROCESS FOR THE SYNTHESIS OF 1-SUBSTITUTED IMIDAZOLE-5-CARBOXYLIC ACIDS AND CARBOXYLIC ACID DERIVATIVES

The invention relates to a novel process for the synthesis of 1-substituted imidazole-5-carboxylic acids and carboxylic acid derivatives and to novel intermediates for carrying out this process and to processes for the preparation of the novel intermediates.

Imidazoles of the formula I are valuable herbicidal and plant growth regulating active ingredients. These herbicidally active imidazoles are covered by the generic formula I

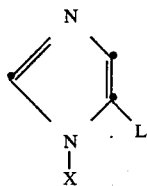

in which
L and X represent $L^1$ and $X^1$; $L^2$ and $X^2$; $L^3$ and $X^3$; or $L^4$ and $X^4$; respectively, and
$L^1$ represents $COOR^1$; $CONR^2R^3$; $CONR^4NHR^3$; or CN;
$R^1$ represents hydrogen; $C_1$–$C_7$-alkyl; $C_3$–$C_7$-alkenyl; $C_3$–$C_7$-alkynyl; $C_3$–$C_7$-cycloalkyl; $C_1$–$C_7$-alkoxy-$C_1$–$C_7$-alkyl; or aryl-$C_1$–$C_5$-alkyl; the radicals $R^2$, $R^3$ and $R^4$, independently of one another, each represents hydrogen; $C_1$–$C_5$-alkyl; $C_3$–$C_5$-alkenyl; $C_3$–$C_5$-alkynyl; $C_3$–$C_7$-cycloalkyl; aryl; or $C_1$–$C_5$-alkyl substituted by aryl, $C_3$–$C_7$-cycloalkyl, $C_3$–$C_7$-cycloalkoxy, $C_1$–$C_5$-alkoxy, hydroxy, carboxy or by $C_1$–$C_5$-alkoxycarbonyl; or
$R^2$ and $R^3$, together with the nitrogen atom to which they are bonded, represent a piperidinyl, pyrrolidinyl, 2-oxopiperidinyl, 2-oxopyrrolidinyl, morpholinyl, thiomorpholinyl, piperazinyl or 4-($C_1$–$C_4$)-alkyl-piperazinyl ring that is unsubstituted or is substituted by from 1 to 3 $C_1$–$C_5$-alkyl groups;
$X^1$ represents 1-indanyl, 1-tetrahydronaphthalenyl, 5-benzocycloheptanyl, 4-tetrahydrobenzothienyl, 4-tetrahydrobenzofuranyl, 5-tetrahydroquinolinyl, 5-tetrahydroisoquinolinyl, 8-tetrahydroquinolinyl, 8-tetrahydroisoquinolinyl, 9,10-dihydro-9-anthracenyl, 9H-fluoren-9-yl, 5-dibenzo[a,d]cycloheptenyl, 5-dibenzo[a,d]cycloheptanyl or 1-dihydronaphthalenyl, each of which is unsubstituted or is substituted up to six times by the same or different substituents selected from $C_1$–$C_5$-alkyl, aryl-$C_1$–$C_5$-alkyl, diaryl-$C_1$–$C_5$-alkyl, $C_1$–$C_5$-alkoxy, halogen, $C_3$–$C_7$-alkenyl, amino, nitro, $C_1$–$C_5$-alkylcarbonylamino, trifluoromethyl and difluoromethoxy, or in which two geminally bonded substituents, together with the carbon atom to which they are bonded, form a $C_3$–$C_7$-spirocycloalkyl group, or in which two substituents together represent a $C_1$–$C_5$-alkylene or $C_5$–$C_7$-cycloalkylene group, it being possible for this alkylene or cycloalkylene group in turn optionally to be substituted up to twice by the same or different substituents selected from $C_1$–$C_5$-alkyl, aryl-$C_1$–$C_5$-alkyl, diaryl-$C_1$–$C_5$-alkyl, $C_1$–$C_5$-alkoxy, halogen, $C_3$–$C_7$-alkenyl, trifluoromethyl, difluoromethoxy and aryl; or $X^1$ represents the group

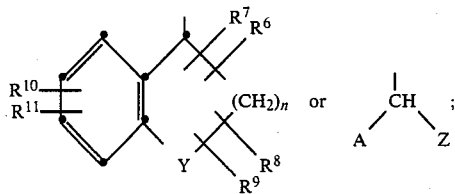

n represents 0; 1; or 2;
Y represents a group $-CH_2S(O)_m-$ or $-CH_2-N(R^{12})-$ in which the hetero atom is bonded to the benzene ring carbon atom and in which m represents 0, 1 or 2;
$R^6$, $R^7$, $R^8$ and $R^9$, independently of one another, each represents hydrogen; $C_1$–$C_5$-alkyl; aryl-$C_1$–$C_5$-alkyl; diaryl-$C_1$–$C_5$-alkyl; $C_1$–$C_5$-alkoxy; halogen; $C_3$–$C_7$-alkenyl; trifluoromethyl; difluoromethoxy; or aryl; or
$R^6$ and $R^7$ together represent a fused benzene radical which can optionally be substituted up to twice by $C_1$–$C_5$-alkyl, $C_1$–$C_5$-alkoxy, halogen, mono- to tri-halo-substituted $C_1$–$C_5$-alkyl, mono- to tri-halo-substituted $C_1$–$C_5$-alkoxy, nitro, amino or by $-NH-CO-M$; or
$R^6$ and $R^7$, together with the carbon atom to which they are geminally bonded, represent a spirocyclic $C_3$–$C_7$-ring; or
$R^6$ and $R^7$ together represent a $C_1$–$C_5$-alkylene or $C_5$–$C_7$-cycloalkylene group which can optionally be substituted up to twice by the same or different substituents selected from $C_1$–$C_5$-alkyl, aryl-$C_1$–$C_5$-alkyl, $C_1$–$C_5$-alkoxy, halogen, $C_3$–$C_7$-alkenyl, trifluoromethyl, difluoromethoxy and aryl; and
$R^{10}$ and $R^{11}$, independently of one another, each represents hydrogen; $C_1$–$C_5$-alkyl; $C_1$–$C_5$-alkoxy; halogen; trifluoromethyl; difluoromethoxy; cyano; nitro; amino; mono-$C_1$–$C_5$-alkylamino; di-$C_1$–$C_5$-alkylamino; or $-NH-CO-M$; and
$R^{12}$ represents hydrogen; $C_1$–$C_5$-alkyl; $C_1$–$C_5$-alkanoyl; or 4-methylphenylsulphonyl; and
A represents hydrogen; $C_3$–$C_7$-cycloalkyl optionally substituted up to twice by $C_1$–$C_5$-alkyl; $C_1$–$C_7$-alkyl optionally substituted by $C_1$–$C_7$-alkoxy or by aryl; $C_1$–$C_7$-alkyl substituted by a $C_1$–$C_7$-alkoxy and by an aryl radical; or pyridinyl, pyrimidinyl, naphthalenyl, furanyl or thiophenyl, each of which is unsubstituted or is substituted up to twice by the same or different substituents selected from $C_1$–$C_5$-alkyl, $C_1$–$C_5$-alkoxy, halogen, nitro, amino, mono-$C_1$–$C_5$-alkylamino, di-$C_1$–$C_5$-alkylamino, $-NH-CO-M$, cyano, trifluoromethyl and difluoromethoxy;
and within the scope of the definition of A, aryl represents phenyl, pyridinyl, pyrimidinyl, naphthalenyl, furanyl or thiophenyl, and this radical can be substituted up to twice, or in the case when aryl is phenyl up to three times, by the same or different substituents selected from $C_1$–$C_5$-alkyl, $C_1$–$C_5$-alkoxy, halogen, nitro, amino, mono-$C_1$–$C_5$-alkyl amino, di-$C_1$–$C_5$-alkylamino, $-NH-CO-M$, cyano, trifluoromethyl and difluoromethoxy; and
Z represents naphthalenyl, thiophenyl, furanyl, pyrimidinyl, phenyl or pyridinyl, each of which is unsubstituted or is substituted up to three times by the same or different substituents selected from $C_1$–$C_5$-alkyl, $C_1$–$C_5$-alkoxy, halogen, cyano, nitro, amino, mono- $C_1-C_5$-alkylamino, di-$C_1-C_5$-alkylamino, —NH—CO—M, trifluoromethyl and difluoromethoxy; and M represents $C_1-C_5$-alkyl; and aryl within the scope of the above definitions of the radicals X and L may also represent a phenyl radical that is unsubstituted or is substituted up to three times by the same or different substituents selected from $C_1-C_5$-alkyl, $C_1-C_5$-alkoxy and halogen; and $L^2$ represents CO—D—$R^{13}$;

D represents O; or $NR^{13}$;

$R^{13}$ represents hydrogen; phenyl; $C_3-C_6$-alkenyl; or $C_1-C_{12}$-alkyl that is unsubstituted or is substituted up to three times by the same or different substituents selected from $C_1-C_6$-alkoxy, $C_1-C_3$-dialkylamino and halogen; and $R^{13}$, when D is O, additionally represents a cation of a metal of group I, II or VII of the Periodic Table or of ammonium; and $X^2$ represents a radical

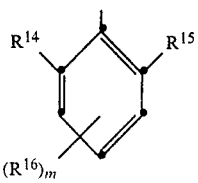

m represents 0, 1, 2 or 3; and $R^{14}$ and $R^{15}$, independently of one another, each represent $C_1-C_4$-alkyl;

$R^{16}$ represents the same or different radicals selected from the group comprising $C_1-C_4$-alkyl, $C_1-C_4$-alkoxy and halogen;

$L^3$ represents CN: $COOR^{17}$; or $CONR^{18}R^{19}$; and $R^{17}$ represents unsubstituted or halo-substituted $C_1-C_7$-alkyl, $C_3-C_7$-alkenyl, $C_3-C_7$-alkynyl, $C_1-C_7$-alkoxy-$C_1-C_7$-alkyl, $C_3-C_7$-cycloalkyl or aryl-$C_1-C_5$-alkyl; and $R^{18}$ and $R^{19}$, which may be the same or different, represent hydrogen; $C_1-C_4$-alkyl; $C_3-C_7$-alkenyl; $C_3-C_7$-alkynyl; or $C_1-C_7$-alkoxy-$C_1-C_7$-alkyl; or $R^{18}$ and $R^{19}$, together with the nitrogen atom to which they are bonded, represent a saturated or unsaturated three- to seven-membered ring that contains up to three hetero atoms selected from the group comprising O, N and S and that is unsubstituted or is substituted by ($C_1-C_4$)-alkyl or by halogen and may contain a carbonyl group; and $X^3$ represents a radical

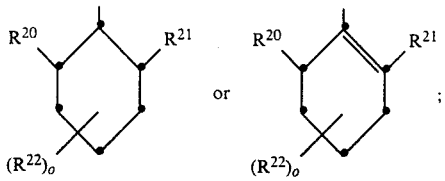

o represents from 0 to 6;

$R^{20}$ and $R^{21}$, independently of one another, each represents hydrogen or $C_1-C_4$-alkyl; and $R^{22}$ represents, independently of any other, $C_1-C_4$-alkyl; $C_1-C_4$-alkoxy; $C_1-C_4$-hydroxyalkyl, $C_1-C_4$-alkoxy-$C_1-C_4$-alkyl; or halogen; and $L^4$ represents CO—$R^{23}$; or CN;

$R^{23}$ represents hydroxy; $C_1-C_6$-alkoxy; hydroxy-($C_2-C_6$)-alkoxy; ($C_2-C_6$)-alkoxyalkoxy; amino; $C_1-C_6$-alkylamino; di-($C_1-C_6$)-alkylamino; di-($C_1-C_6$)-alkylamino-($C_1-C_3$)-alkylamino; $C_1-C_3$-alkoxyamino; anilino; N-pyrrolidino; N-piperidino; N-morpholino; hydrazino; N'-($C_1-C_3$)-alkylhydrazino; N,N'-dimethylhydrazino; or N'-phenylhydrazino; and $X^4$ represents the radical

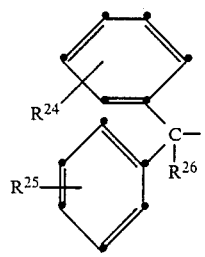

and $R^{24}$ and $R^{25}$, which may be the same or different, represent hydrogen; halogen; $C_1-C_3$-alkyl; trifluoromethyl; hydroxy; $C_1-C_3$-alkoxy; halo-($C_1-C_3$)-alkoxy; $C_1-C_3$-alkylthio; cyano; nitro; or acetamido; and $R^{26}$ represents hydrogen; or phenyl.

Imidazole-5-carboxylic acids and carboxylic acid derivatives having herbicidal and plant growth regulating activity that are substituted in the 1-position of the imidazole system by radicals having a large spatial configuration are known.

For example, compounds of the formula I in which X and L represent $X^1$ and $L^1$ are described in European patent application Nos. EP-A-207 563, EP-A-240 050 and EP-A-234 656. Compounds of the formula I in which X and L represent $X^2$ and $L^2$ are the subject of EP-A-137 868, whilst the radicals $X^3$ and $L^3$ are known from EP-A-199 206 and the radicals $X^4$ and $L^4$ are disclosed in EP-A-373.

With regard to the scope of the definition of the radicals X and L and the preferred forms and the individual compounds of the formula I, reference is made expressly to the above-mentioned publications.

A common feature of the compounds of the formula I is that they carry at the nitrogen atom in the 1-position of the imidazole system a substituent having a large spatial configuration which, for reasons of steric interaction, renders difficult the synthesis of the imidazole system by methods known per se (starting from acyclic precursors, by imidazole ring-closure reactions). Steric interaction also influences the synthesis of compounds of the formula I by substitution reactions starting from imidazolecarboxylic acids unsubstituted in the 1-position and suitable compounds of the formula X—Y in which Y represents a leaving group.

The processes known from the prior art for the synthesis of the imidazoles are—insofar as the synthesis proceeds via an imidazole ring-closure—variants of the Paal-Knorr synthesis of imidazoles, that is to say that 1,4-dicarbonyl compounds in which the substituents X and L are already bonded at the corresponding positions of the acyclic educts are cyclised with ammonia or acid amides to form the imidazoles of the formula I. In many cases the synthesis of the open-chain 1,4-dicarbonyl compounds that are required for those variants is expensive. In addition, with this reaction procedure it must be accepted that with the substituent L a further reactive centre will be present in the acyclic educt, which centre is itself capable of reacting with the ammonia or amine required for the ring-closure.

The afore-mentioned patent publications also describe a further process for the manufacture of the imidazoles according to the application, which process uses amines of the formula X—NH$_2$ as starting materials and first of all converts these by reaction with chloroacetic acid esters into the corresponding glycine derivatives. These are then twice subjected to formylation with formic acid esters (at the nitrogen atom and at the methylene group of the glycine fragment) and subsequently cyclised with thiocyanic acid. In this manner there are first formed 2-mercaptoimidazoles substituted in the 5-position by L and in the 1-position by X from which the mercapto group is removed by catalytic processes. This process is especially unsuitable when the group X for its part contains groups that are unstable towards the desulphuration, such as, for example, in the case of the compounds of the formula I in which X represents a sulphur-containing substituent.

This process is also described in J. Amer. Chem. Soc. 71 (1949) 644–647 and 2444–2448.

The syntheses of compounds of the formula I known from the prior art are therefore unsatisfactory in terms of practicability, availability of the intermediates, general practicability, and also purity and yield of the end products.

The problem underlying the invention is to provide a process that is improved in comparison with the known processes.

According to the invention this problem is solved by a process for the preparation of imidazoles of the formula I

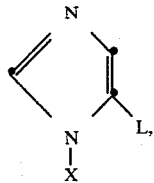

(I)

in which
L and X represent L$^1$ and X$^1$; L$^2$ and X$^2$; L$^3$ and X$^3$; or L$^4$ and X$^4$; respectively and L$^1$ represents COOR$^1$; CONR$^2$R$^3$; CONR$^4$NHR$^3$; or CN;

R$^1$ represents hydrogen; C$_1$–C$_7$-alkyl; C$_3$–C$_7$-alkenyl; C$_3$–C$_7$-alkynyl; C$_3$–C$_7$-cycloalkyl; C$_1$–C$_7$-alkoxy-C$_1$–C$_7$-alkyl; or aryl-C$_1$–C$_5$-alkyl; the radicals R$^2$, R$^3$ and R$^4$, independently of one another, each represents hydrogen; C$_1$–C$_5$-alkyl; C$_3$–C$_5$-alkenyl; C$_3$–C$_5$-alkynyl; C$_3$–C$_7$-cycloalkyl; aryl; or C$_1$–C$_5$-alkyl substituted by aryl, C$_3$–C$_7$-cycloalkyl, C$_3$–C$_7$-cycloalkoxy, C$_1$–C$_5$-alkoxy, hydroxy, carboxy or by C$_1$–C$_5$-alkoxycarbonyl; or R$^2$ and R$^3$, together with the nitrogen atom to which they are bonded, represent a piperidinyl, pyrrolidinyl, 2-oxopiperidinyl, 2-oxopyrrolidinyl, morpholinyl, thiomorpholinyl, piperazinyl or 4-(C$_1$–C$_4$)-alkylpiperazinyl ring that is unsubstituted or is substituted by from 1 to 3 C$_1$–C$_5$-alkyl groups;

X$^1$ represents 1-indanyl, 1-tetrahydronaphthalenyl, 5-benzocycloheptanyl, 4-tetrahydrobenzothienyl, 4-tetrahydrobenzofuranyl, 5-tetrahydroquinolinyl, 5-tetrahydroisoquinolinyl, 8-tetrahydroquinolinyl, 8-tetrahydroisoquinolinyl, 9,10-dihydro-9-anthracenyl, 9H-fluoren-9-yl, 5-dibenzo[a,d]cycloheptenyl, 5-dibenzo[a,d]cycloheptanyl or 1-dihydronaphthalenyl, each of which is unsubstituted or is substituted up to six times by the same or different substituents selected from C$_1$–C$_5$-alkyl, aryl-C$_1$–C$_5$-alkyl, diaryl-C$_1$–C$_5$-alkyl, C$_1$–C$_5$-alkoxy, halogen, C$_3$–C$_7$-alkenyl, amino, nitro, C$_1$–C$_5$-alkylcarbonyl amino, trifluoromethyl and difluoromethoxy, or in which two geminally bonded substituents, together with the carbon atom to which they are bonded, form a C$_3$–C$_7$-spirocycloalkyl group, or in which two substituents together represent a C$_1$–C$_5$-alkylene or C$_5$–C$_7$-cycloalkylene group, it being possible for this alkylene or cycloalkylene group in turn optionally to be substituted up to twice by the same or different substituents selected from C$_1$–C$_5$-alkyl, aryl-C$_1$–C$_5$-alkyl, diaryl-C$_1$–C$_5$-alkyl, C$_1$–C$_5$-alkoxy, halogen, C$_3$–C$_7$-alkenyl, trifluoromethyl, difluoromethoxy and aryl; or X$^1$ represents the group

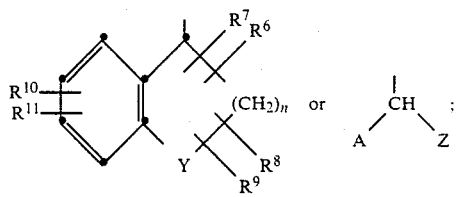

n represents 0; 1; or 2;

Y represents a group —CH$_2$S(O)$_m$— or —CH$_2$—N(R$^{12}$)— in which the hetero atom is bonded to the benzene ring carbon atom and in which m represents 0, 1 or 2;

R$^6$, R$^7$, R$^8$ and R$^9$, independently of one another, each represents hydrogen; C$_1$–C$_5$-alkyl; aryl-C$_1$–C$_5$-alkyl; diaryl-C$_1$–C$_5$-alkyl; C$_1$–C$_5$-alkoxy; halogen; C$_3$–C$_7$-alkenyl; trifluoromethyl; difluoromethoxy; or aryl; or R$^6$ and R$^7$ together represent a fused benzene radical which can optionally be substituted up to twice by C$_1$–C$_5$-alkyl, C$_1$–C$_5$-alkoxy, halogen, mono- to tri-halo-substituted C$_1$–C$_5$-alkyl, mono- to tri-halo-substituted C$_1$–C$_5$-alkoxy, nitro, amino or by —NH—CO—M; or R$^6$ and R$^7$, together with the carbon atom to which they are geminally bonded, represent a spirocyclic C$_3$–C$_7$-ring; or R$^6$ and R$^7$ together represent a C$_1$–C$_5$-alkylene or C$_5$–C$_7$-cycloalkylene group which can optionally be substituted up to twice by the same or different substituents selected from C$_1$–C$_5$-alkyl, aryl-C$_1$–C$_5$-alkyl, C$_1$–C$_5$-alkoxy, halogen, C$_3$–C$_7$-alkenyl, trifluoromethyl, difluoromethoxy and aryl; and R$^{10}$ and R$^{11}$, independently of one another, each represents hydrogen; C$_1$–C$_5$-alkyl; C$_1$–C$_5$-alkoxy; halogen; trifluoromethyl; difluoromethoxy; cyano; nitro; amino; mono-C$_1$–C$_5$-alkylamino; di-C$_1$–C$_5$-alkylamino; or —NH—CO—M; and R$^{12}$ represents hydrogen; C$_1$–C$_5$-alkyl; C$_1$–C$_5$-alkanoyl; or 4-methylphenylsulphonyl; and A represents hydrogen; C$_3$–C$_7$-cycloalkyl optionally substituted up to twice by C$_1$–C$_5$-alkyl; C$_1$–C$_7$-alkyl optionally substituted by C$_1$–C$_7$-alkoxy or by aryl; C$_1$–C$_7$-alkyl substituted by a C$_1$–C$_7$-alkoxy and by an aryl radical; or pyridinyl, pyrimidinyl, naphthalenyl, furanyl or thiophenyl, each of which is unsubstituted or is substituted up to twice by the same or different substituents selected from $C_1-C_5$-alkyl, $C_1-C_5$-alkoxy, halogen, nitro, amino, mono-$C_1-C_5$-alkylamino, di-$C_1-C_5$-alkylamino, —NH—CO—M, cyano, trifluoromethyl and difluoromethoxy;

and within the scope of the definition of A, aryl represents phenyl, pyridinyl, pyrimidinyl, naphthalenyl, furanyl or thiophenyl, and this radical can be substituted up to twice, or in the case when aryl is phenyl up to three times, by the same or different substituents selected from $C_1-C_5$-alkyl, $C_1-C_5$-alkoxy, halogen, nitro, amino, mono-$C_1-C_5$-alkylamino, di-$C_1-C_5$-alkylamino, —NH—CO—M, cyano, trifluoromethyl and difluoromethoxy; and Z represents naphthalenyl, thiophenyl, furanyl, pyrimidinyl, phenyl or pyridinyl, each of which is unsubstituted or is substituted up to three times by the same or different substituents selected from $C_1-C_5$-alkyl, $C_1-C_5$-alkoxy, halogen, cyano, nitro, amino, mono-$C_1-C_5$-alkylamino, di-$C_1-C_5$-alkylamino, —NH—CO—M, trifluoromethyl and difluoromethoxy; and M represents $C_1-C_5$-alkyl; and aryl within the scope of the above definitions of the radicals X and L may also represent a phenyl radical that is unsubstituted or is substituted up to three times by the same or different substituents selected from $C_1-C_5$-alkyl, $C_1-C_5$-alkoxy and halogen; and $L^2$ represents $CO-D-R^{13}$;

D represents O; or $NR^{13}$;

$R^{13}$ represents hydrogen; phenyl; $C_3-C_6$-alkenyl; or $C_1-C_{12}$-alkyl that is unsubstituted or is substituted up to three times by the same or different substituents selected from $C_1-C_6$-alkoxy, $C_1-C_3$-dialkylamino and halogen; and $R^{13}$, when D is O, additionally represents a cation of a metal of group I, II or VII of the Periodic Table or of ammonium; and $X^2$ represents a radical

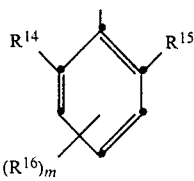

m represents 0, 1, 2 or 3; and $R^{14}$ and $R^{15}$, independently of one another, each represents $C_1-C_4$-alkyl;

$R^{16}$ represents the same or different radicals selected from the group comprising $C_1-C_4$-alkyl, $C_1-C_4$-alkoxy and halogen;

$L^3$ represents CN; $COOR^{17}$; or $CONR^{18}R^{19}$; and $R^{17}$ represents unsubstituted or halo-substituted $C_1-C_7$-alkyl, $C_3-C_7$-alkenyl, $C_3-C_7$-alkynyl, $C_1-C_7$-alkoxy-$C_1-C_7$-alkyl, $C_3-C_7$-cycloalkyl or aryl-$C_1-C_5$-alkyl; and $R^{18}$ and $R^{19}$, which may be the same or different, represent hydrogen; $C_1-C_4$-alkyl; $C_3-C_7$-alkenyl; $C_3-C_7$-alkynyl; or $C_1-C_7$-alkoxy-$C_1-C_7$-alkyl; or $R^{18}$ and $R^{19}$, together with the nitrogen atom to which they are bonded, represent a saturated or unsaturated three- to seven-membered ring that contains up to three hetero atoms selected from the group comprising O, N and S and that is unsubstituted or is substituted by ($C_1-C_4$)-alkyl or by halogen and may contain a carbonyl group; and $X^3$ represents a radical

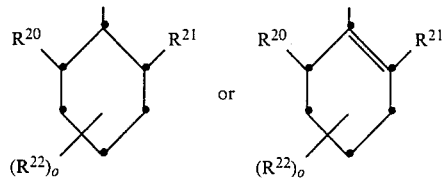

o represents from 0 to 6;

$R^{20}$ and $R^{21}$, independently of one another, each represents hydrogen or $C_1-C_4$-alkyl; and $R^{22}$ represents, independently of any other, $C_1-C_4$-alkyl; $C_1-C_4$-alkoxy; $C_1-C_4$-hydroxyalkyl; $C_1-C_4$-alkoxy-$C_1-C_4$-alkyl; or halogen; and $L^4$ represents $CO-R^{23}$; or CN;

$R^{23}$ represents hydroxy; $C_1-C_6$-alkoxy; hydroxy-($C_2-C_6$)-alkoxy; ($C_2-C_6$)-alkoxyalkoxy; amino; $C_1-C_6$-alkylamino; di-($C_1-C_6$)-alkylamino; di-($C_1-C_6$)-alkylamino-($C_1-C_3$)-alkylamino; $C_1-C_3$-alkoxyamino; anilino; N-pyrrolidino; N-piperidino; N-morpholino; hydrazino; N'-($C_1-C_3$)-alkylhydrazino; N,N'-dimethylhydrazino; or N'-phenylhydrazino; and $X^4$ represents the radical

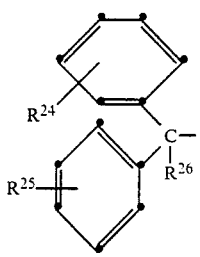

and $R^{24}$ and $R^{25}$, which may be the same or different, represent hydrogen; halogen; $C_1-C_3$-alkyl; trifluoromethyl; hydroxy; $C_1-C_3$-alkoxy; halo-($C_1-C_3$)-alkoxy; $C_1-C_3$-alkylthio; cyano; nitro; or acetamido; and $R^{26}$ represents hydrogen; or phenyl;

characterised in that an N-cyanoformamidine of the formula II

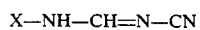

$$X-NH-CH=N-CN \qquad (II),$$

in which X has the definition given above, is N-alkylated with a compound of the formula III $$Z-CH_2-L \qquad (III),$$

in which L has the definition given above and Z represents a nucleofugal group, to form a compound of the formula IV

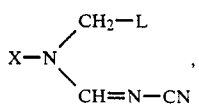

$$(IV)$$

and IV is cyclised under the action of bases to form a 4-aminoimidazole of the formula V

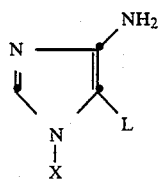
(V)

and the aminoimidazole V is reduced to form an imidazole of the formula I.

The 4-aminoimidazoles of the formula V are preferably reduced in a two-stage process by converting a 4-aminoimidazole of the formula V

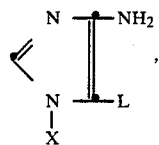
(V)

in which X and L have the definitions given above, into a diazonium salt of the formula VI

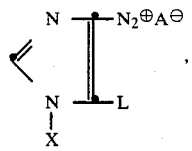
(VI)

in which A represents an anion, and reacting to form imidazoles of the formula I with nitrogen being removed. The invention relates also to these processes and also to the novel diazonium salts of the formula VI.

Within the scope of the definition used herein, the generic terms include, for example, the following specific individual substituents, but this list does not represent a limitation of the invention.

Alkyl includes the structurally isomeric alkyls within the scope of the number of carbon atoms indicated in each particular case, such as methyl, ethyl, n-propyl, isopropyl, n-butyl, sec.-butyl, isobutyl, tert.-butyl, the isomeric pentyls, such as, for example, tert.-pentyl (1,1-dimethylpropyl), isopentyl (1-ethylpropyl), and so on, and also the isomeric hexyl and heptyl groups.

Halogen is fluorine, chlorine, bromine and iodine, preferably fluorine, chlorine and bromine, especially fluorine and chlorine.

Haloalkyl is intended to indicate alkyl groups falling within the scope of the definition in each particular case that are partly or fully substituted by the same or different halogen atoms, such as, for example, 2,2,2-trifluoroethyl, trifluoromethyl, difluoromethyl, chlorodifluoromethyl, fluorochloromethyl, dichloromethyl, chloromethyl, trichloromethyl, and so on.

Alkenyl includes the structural isomers as well as the cis-transisomers within the scope of the number of carbon atoms indicated in each particular case, such as the propenyl, butenyl, pentenyl, hexenyl and heptenyl radicals.

Alkynyl includes the structurally isomeric compounds likewise within the scope of the number of carbon atoms indicated in any particular case, such as, for example, the propynyl, butynyl, pentynyl, hexynyl and heptynyl radicals.

Where alkenyl or alkynyl radicals are bonded to an oxygen or nitrogen atom belonging to an ester or amide group, these radicals are preferably bonded to the hetero atom via a saturated carbon atom.

$C_3$–$C_7$-cycloalkyl includes cyclopropyl, cyclobutyl, cyclopentyl, cyclohexyl and cycloheptyl.

Haloalkoxy includes, within the scope of the definition in each particular case, radicals substituted preferably by fluorine, chlorine and bromine, such as, for example, trifluoromethoxy, trichloromethoxy, dibromomethoxy, difluorochloromethoxy, dichloromethoxy, 2,2,1-trichloroethoxy, 2,2,1-trifluoroethoxy, and so on.

In the other substituents, which are composed of several basic elements, the constituents parts can be freely selected within the scope of the definition and have inter alia the above meanings.

The compounds according to the invention can also be in the form of optical isomers and the invention relates also to these.

In cases where the substituent X is bonded by an asymmetrically substituted carbon atom to the imidazole radical according to the invention, both the compounds of the formula I having the R-configuration and those having the S-configuration are included.

Furthermore, the molecules of the formula I according to the invention may contain further asymmetric centres which in their individual intercombinations are also included. The invention therefore includes all diastereoisomers and enantiomers that can be derived from the formula I.

Especially, the α-carbon atom in the position adjacent to the carbon atom carrying the imidazole system, or the β-carbon atom adjacent thereto can each be monosubstituted, in which case these substituents can be in the cis or trans position relative to one another or relative to the imidazole system. These cis-, trans-isomers are also included.

Finally, it should be stated that the process according to the invention is most suitable for the synthesis of chiral systems of the formula I (and of the associated intermediates II, IV, V and VI), since the construction of the imidazole system is carried out without any alteration of the configuration in the molecule constituents X and L. It is thus possible to produce from the optically active educts of the formula VIII and/or III the respective optically active end products of the formula I without the optical activity originating from the educts being lost in the course of the reaction.

The definitions of the end compounds of the formula I are given in more detail in European patent application Nos. EP-A-373, EP-A-207 563, EP-A-240 050, EP-A-234 656, EP-A-137 868 and EP-A-199 206, and reference is made to these.

The compounds of the formulae II, IV, V and VI are novel. They represent valuable intermediate compounds for the synthesis of the herbicidally active end compounds of the formula I. The invention relates also to the novel substances of the formulae II, IV, V and VI and to processes for their preparation and to their use for the preparation of the respective secondary products in accordance with the following formula scheme:

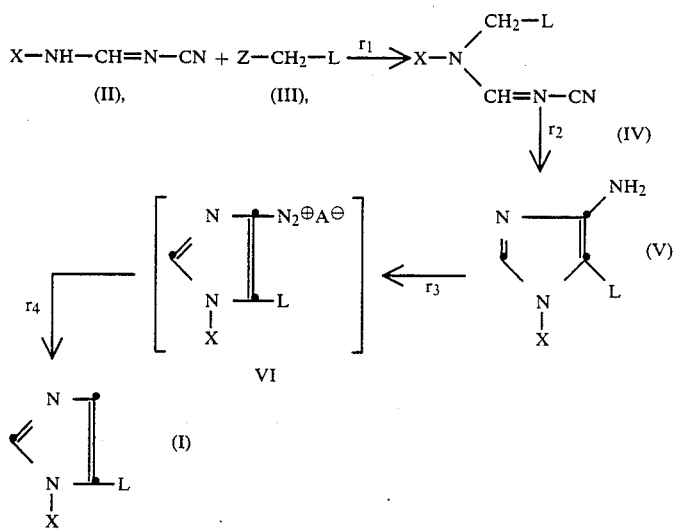

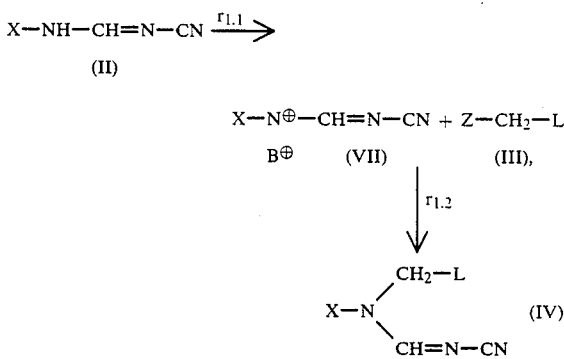

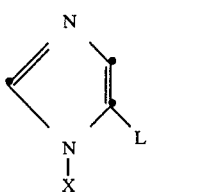

The alkylation reaction $r_1$ is preferably carried out in two steps, by first deprotonating the N-cyanoformamidine by means of a base to form a salt of the formula VII and then alkylating at the nitrogen atom with a compound of the formula III in accordance with the following reaction equation:

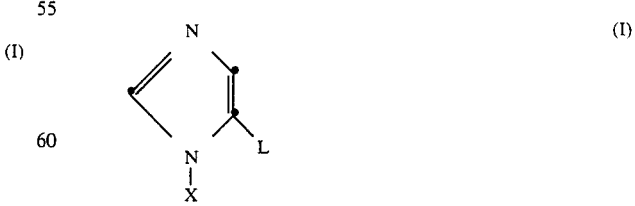

Reaction steps $r_{1.1}$ and $r_{1.2}$ can be carried out one after another, in two separate stages, or simultaneously as a "one-pot process".

The process according to the invention can preferably be used for the preparation of those compounds of the formula I which are singled out as being preferred or especially preferred or are mentioned as individual compounds in EP-A-373, EP-A-207 563, EP-A-240 050, EP-A-234 656, EP-A-137 868 and EP-A-199 206.

Furthermore, the process according to the invention is preferred in the case of compounds of the formula I in which L represents $COOR^1$; $CONR^2R^3$; or CN; and $R^1$ represents hydrogen; $C_1$–$C_7$-alkyl; $C_3$–$C_7$-alkenyl; $C_3$–$C_7$-alkynyl; $C_3$–$C_7$-cycloalkyl; $C_1$–$C_7$-alkoxy-$C_1$–$C_7$-alkyl; or aryl-$C_1$–$C_5$-alkyl; the radicals $R^2$, $R^3$ and $R^4$, independently of one another, each represents hydrogen; $C_1$–$C_5$-alkyl; $C_3$–$C_5$-alkenyl; $C_3$–$C_5$-alkynyl; $C_3$–$C_7$-cycloalkyl; aryl; or $C_1$–$C_5$-alkyl substituted by aryl, $C_3$–$C_7$-cycloalkyl, $C_3$–$C_7$-cycloalkoxy, $C_1$–$C_5$-alkoxy, hydroxy, carboxy or by $C_1$–$C_5$-alkoxycarbonyl; or $R^2$ and $R^3$, together with the nitrogen atom to which they are bonded, represent a piperidinyl, pyrrolidinyl, 2-oxopiperidinyl, 2-oxopyrrolidinyl, morpholinyl, thiomorpholinyl, piperazinyl or 4-($C_1$–$C_4$)-alkylpiperazinyl ring that is unsubstituted or is substituted by from 1 to 3 $C_1$–$C_5$-alkyl groups; and X represents 1,2,3,4-tetrahydronaphthalen-1-yl, indan-1-yl, phenyl, diphenylmethyl, benzocycloheptan-5-yl, 4,5,6,7-tetrahydrobenzo[b]thiophen-4-yl, 4,5,6,7-tetrahydrobenzo[b]furan-4-yl, 5,6,7,8-tetrahydroquinolin-5-yl, 5,6,7,8-tetrahydroisoquinolin-5-yl, 5,6,7,8-tetrahydroquinolin-8-yl, 5,6,7,8-tetrahydroisoquinolin-8-yl, 9,10-dihydroanthracen-9-yl, 9H-fluoren-9-yl, dibenzo[a,d]cyclohepten-5-yl, dibenzo[a,d]cycloheptan-5-yl, 1,2-dihydronaphthalen-1-yl, chroman-4-yl or thiochroman-4-yl, each of which is unsubstituted or is substituted up to three times by $C_1$–$C_4$-alkyl or by halogen or in which two geminally bonded substituents, together with the carbon atom to which they are bonded, form a $C_3$–$C_6$-spiroalkyl group.

Also preferred are compounds of the formula I in which

X has the definition given above, and

L represents $COOR^1$; CN; or $CNR^2R^3$;

$R^1$ represents $C_1$–$C_4$-alkyl; $C_3$–$C_6$-cycloalkyl; or $C_3$–$C_6$-alkenyl; and $R^2$ and $R^3$, independently of one another, each represents hydrogen or $C_1$–$C_4$-alkyl.

The process according to the invention is especially preferred for the preparation of compounds of the formula I

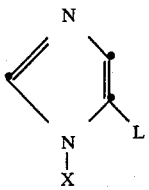  (I)

in which

L represents $COOR^1$; CN; or $CNR^2R^3$; and $R^1$ represents $C_1$–$C_4$-alkyl; $C_3$–$C_6$-alkenyl; or $C_3$–$C_6$-cyclo-alkyl;

$R^2$ and $R^3$, independently of one another, each represents hydrogen or $C_1$–$C_4$-alkyl; and X represents 2,2-dimethyl-1,2,3,4-tetrahydronaphthalen-1-yl, 2,2-dimethylindan-1-yl, 2,6-dimethylphenyl, diphenylmethyl, indan-1-yl, 2-methylindan-1-yl, cis-2-methylindan-1-yl, trans-2-methylindan-1-yl, 1,2,3,4-tetrahydronaphthalen-1-yl, 2-methyl-1,2,3,4-tetrahydronaphthalen-1-yl, cis-2-methyl-1,2,3,4-tetrahydronaphthalen-1-yl, trans-2-methyl-1,2,3,4-tetrahydronaphthalen-1-yl, benzocycloheptan-5-yl, 4,5,6,7-tetrahydrobenzo[b]thiophen-4-yl, 4,5,6,7-tetrahydrobenzo[b]furan-4-yl, 5,6,7,8-tetrahydroquinolin-5-yl, 5,6,7,8-tetrahydroisoquinolin-5-yl, 5,6,7,8-tetrahydroquinolin-8-yl, 5,6,7,8-tetrahydroisoquinolin-8-yl, 9,10-dihydroanthracen-9yl, 9H-fluoren-9-yl, dibenzo[a,d]cyclohepten-5-yl, dibenzo[a,d]cycloheptan-5-yl, 1,2-dihydronaphthalen-1-yl, (4-chlorophenyl)-(phenyl)-methyl, 2-ethyl-6-methylphenyl, 2,6-diethylphenyl, 2,6-diisopropylphenyl, 2,4,6-trimethylphenyl, 4-chloro-2,6-dimethylphenyl, 2-ethylindan-1-yl, cis-2-ethylindan-1-yl, trans-2-ethylindan-1-yl, 2propylindan-1-yl, cis-propylindan-1-yl, transpropylindan-1-yl, 2-isopropylindan-1-yl, 2-ethyl-2-methylindan-1-yl, 2-methyl-2-propylindan-1-yl, 2,2-diethylindan-1-yl, 2,2-dipropylindan-1-yl, spiro[cyclopropane-1,2'-indan]-1'-yl, spiro[cyclopentane-1,2'-indan]-1'-yl, spiro[cyclohexane-1,2'-indan]-1'-yl, 2-ethyl-1,2,3,4-tetrahydronaphthalen-1-yl, cis-2-ethyl-1,2,3,4-tetrahydronaphthalen-1-yl, trans-2-ethyl-1,2,3,4-tetrahydronaphthalen-1-yl, 2-propyl-1,2,3,4-tetra hydronaphthalen-1-yl, cis-2-propyl-1,2,3,4-tetrahydronaphthalen-1yl, trans-2-propyl-1,2,3,4-tetrahydronaphthalen-1-yl, 2-ethyl-2-methyl-1,2,3,4-tetrahydronaphthalen-1-yl, 2-methyl-2-propyl-1,2,3,4-tetrahydronaphthalen-1-yl, 2,2-diethyl-1,2,3,4-tetrahydronaphthalen-1-yl, 2,2-dipropyl-1,2,3,4-tetrahydronaphthalen-1-yl, spiro[cyclopropane-1,2'-(1',2',3',4'-tetrahydronaphthalen)]-1'-yl, spiro[cyclopentane-1,2'-(1',2',3',4'-tetrahydronaphthalen)]-1'-yl, spiro[cyclohexane-1,2'-(1',2',3',4'-tetrahydronaphthalen)]-1'-yl, chroman-4-yl, 3-methylchroman-4-yl, cis-3methylchroman-4-yl, trans-3-methylchroman-4-yl, 3-ethylchroman-4-yl, cis-3-ethylchroman-4-yl, trans-3-ethylchroman-4-yl, 3-propylchroman-4-yl, cis-3-propylchroman-4-yl, trans-3-propylchroman-4-yl, 3-ethyl-3-methylchroman-4-yl, 3-methyl-3-propylchroman-4-yl, 3-isopropylchroman-4-yl, cis-3-isopropylchroman-4-yl, trans-3-isopropylchroman-4-yl, 3,3-dimethylchroman-4-yl, 3,3-diethylchroman-4-yl, 3,3-dipropylchroman-4-yl, spiro-[cyclopropane-1,3'-chroman]-4'-yl, spiro[cyclopentane-1,3'-chroman]-4'-yl, spiro[cyclohexane-1,3'-chroman]-4'-yl, 2-methylchroman-4-yl, cis-2-methylchroman-4-yl, trans-2-methylchroman-4-yl, 2-ethylchroman-4-yl, cis-2-ethylchroman-4-yl, trans-2-ethylchroman-4-yl, 2-propylchroman-4-yl, cis-2-propylchroman-4-yl, trans-2-propylchroman-4-yl, 2-ethyl-2-methylchroman-4-yl, 2-methyl-2-propylchroman-4-yl, 2-isopropylchroman-4-yl, cis-2-isopropylchroman-4-yl, trans-2-isopropylchroman-4-yl, 2,2-dimethylchroman-4-yl, 2,2-diethylchroman-4-yl, 2,2-dipropylchroman-4-yl, spiro-[cyclopropane-1,2'-chroman]-4'-yl, spiro[cyclopentane-1,2'-chroman]-4'-yl, spiro[cyclohexane-1,2'-chroman[-4'-yl, 2,2-dimethyl-1,2,3,4-tetrahydronaphthalen-1-yl, thiochroman-4-yl, 2,2-dimethylthiochroman-4-yl, 3,3-dimethylthiochroman-4-yl, 2,3-dimethylthiochroman-4-yl, [cis-2,3-dimethyl]thiochroman-4-yl, [trans-2,3-dimethyl]-thiochroman-4-yl, 2-methylthiochroman-4-yl, 2-ethylthiochroman-4-yl, 2-methyl-2-ethylthiochroman-4-yl, 2,2-diethylthiochroman-4-yl, 3,3-diethylthiochroman-4-yl, 3-methyl-3-ethylthiochroman-4-yl, 2,3-dimethylindan-1-yl, [cis-2,3-dimethyl]indan-1-yl, [trans-2,3-dimethyl]indan-1-yl, (+)-2,2-dimethylindan-1-yl, (−)-2,2-dimethylindan-1-yl, (+)-2,2-dimethyl-1,2,3,4-tetrahydronaphthalen-1-yl, (−)-2,2-dimethyl-1,2,3,4-tetrahydronaphthalen-1-yl.

The invention relates also to the novel intermediates of the formulae II, VII, IV, V and VI and to processes for their preparation and to their use for the preparation of compounds of the formula I within the scope of the end products of the formula I mentioned as being preferred or especially preferred.

The process according to the invention will be described in more detail in the following, but the statements made herein do not represent a limitation to the specific means and examples mentioned.

The N-cyanoformamidines of the formula II can be prepared in simple manner analogously to processes known in the literature, for example by condensation of amines (VIII) with cyanamide (IX) and orthoformic acid esters of the formula X.

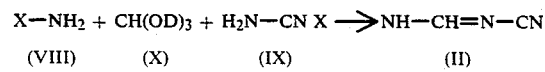

(lit: H. Schäfer and R. Gewald; J. prakt. Chem. 318 [1976], 347–349). In the above equation, D preferably represents a $C_1$–$C_4$-alkyl group.

This condensation reaction can be carried out in a solvent that is inert in the reaction or without solvents preferably in an excess of the orthoester X.

The compounds of the formula II are novel. The invention therefore relates also to a process for the preparation of compounds of the formula II

in which X has the definition given above, characterised in that (a) an amine of the formula VIII

is condensed with an orthoester of the formula X

CH(OD)₃ (X), in which D preferably represents C₁–C₄-alkyl, and cyanamide of the formula IX

H₂NCN (IX), or (b) an amine of the formula VIII

X—NH₂ (VIII)

is condensed with an imido ester of the formula XI

DO—CH=N—CN (XI), in which D represents a C₁–C₄-alkyl group or phenyl, or (c) an imido ester of the formula XII

X—N=CH—OD (XII), in which D represents a C₁–C₄-alkyl group or phenyl, is condensed with cyanamide of the formula IX

H₂NCN (IX).

The reaction is preferably carried out at temperatures of from room temperature to the boiling temperature of the reaction mixture at normal pressure. The temperature range of from 20° to 200° C., especially from 70° to 150° C., is to be regarded as preferred. It is especially advantageous to carry out the operation while simultaneously distilling off the alcohol freed in the reaction. The reaction can likewise be accelerated by the addition of catalytic amounts of mineral acid or organic acids.

The amines of the formula VIII required as starting compound are either known or can be produced according to processes known per se.

If the amino group in VIII is bonded to a saturated carbon atom, the compounds can be prepared, for example, by reduction of the corresponding oxime (for example analogously to Levine J. Org. Chem. 9 [1944] 380; Woods et al., J. Org. Chem. 19 (1954) 1290; Kipling, J. Chem. Soc. 75 152) or by reduction of the corresponding nitro compound (Tranverso., Ann. Chimica 45 [1955] 706). Furthermore, for example, the partially hydrogenated ring systems in the amines of the formula VIII can be obtained by partial reduction of the unsaturated ring systems.

The alkylation of the N-cyanoformamidines II with III (reaction $r_1$) is preferably carried out in the presence of suitable bases, and in a first reaction step the base of the N-cyanoformamidine II is deprotonated to form a salt of the formula VII which

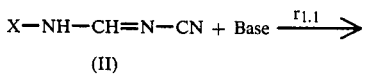

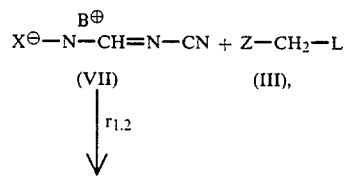

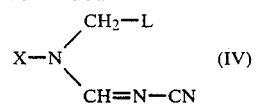

is then alkylated with a compound of the formula III to form a compound of the formula IV. The process can be carried out in two stages, that is to say first the formation of the salt and then the addition of III, or alternatively in a "one-pot process", that is to say salt formation in the presence of III.

In formula VII, the substituent X has the meaning given above, whilst B⊕ represents an equivalent of a cation, preferably an alkali metal ion; alkaline earth metal ion; ammonium or organic ammonium ion.

The reaction can be carried out at temperatures of from 0° C. to the boiling temperature of the reaction mixture in a solvent that is inert in the reaction, and preferably at temperatures of from 0° C. to 50° C., especially at room temperature. Bases suitable for the reaction are:

alkali metal and alkaline earth metal alcoholates, such as, for example, potassium or sodium methoxide, ethoxide or tert.-butoxide; inorganic bases, such as NaOH, KOH, sodium carbonate etc.; alkali metal and alkaline earth metal hydrides, such as sodium hydride; alkali metal amides, such as sodium amide; nitrogen-containing organic bases, such as DABCO (diazabicyclooctane) etc..

Advantageously, the reaction can also be carried out under phase transfer conditions in a two-phase system. Suitable systems of bases, solvents and phase transfer catalysts are known in the literature (for example Dehmlow and Dehmlow, "Phase Transfer Catalysis", Verlag Chemie Weinheim, 1983; W. E. Keller "Phase Transfer Reactions", G. Thieme Verlag Stuttgart, Vol. 1 1986 and Vol. 2 1987).

For carrying out reaction $r_1$, preferably an equimolar amount of base is used. If the reaction is carried out with more than an equimolar amount of base, the compound of the formula IV can cyclise direct to V in accordance with reaction step $r_2$. If it is desirable to isolate the product IV, suitable bases are those of which the base strength is sufficient for the deprotonation of II but not for the cyclisation of V. If an aminoimidazole of the formula V is required directly as product of the reaction, then a base of which the base strength is sufficient for the deprotonation of IV can be used. In that case it is also necessary to use at least an equimolar amount of base (relative to II). Furthermore, the cyclisation reaction $r_2$ is preferably carried out at elevated temperature (preferably from 50° to 150° C.).

In the compound of the formula III, Z represents a nucleofugal group that can be removed under the reaction conditions, such as, for example, halogen (especially chlorine, bromine or iodine) or an aromatic or aliphatic sulphonyl group, such as p-toluenesulphonyl, mesityl or methylsulphonyl.

Individual compounds of the formula III that may be mentioned are: chloro- and bromo-acetic acid methyl ester, ethyl ester, allyl ester, isopropyl ester, propyl ester and cyclopropyl ester; N-methylbromoacetic acid amide, N,N-dimethylbromoacetic acid amide, N-methyl-chloroacetic acid amide and N,N-dimethylchloroacetic acid amide; bromoacetonitrile and chloroacetonitrile.

The compounds of the formula IV that can be prepared in accordance with the above process can be isolated by precipitation, crystallisation, extraction, chromatographic or distillative separating and purification methods. They can, however, also be used directly for the subsequent reaction step r₂ without isolation of the pure substance.

The cyclisation of the N,N-disubstituted N'-cyanoformamidines IV in accordance with reaction step r₂ is effected under the action of bases in a solvent that is inert in the reaction analogously to processes known in the literature (DD-118 640; K. Gewald and G. Heinhold, Monatsh. für Chemie, 107 (1976) 1413; Comprehensive Heterocyclic Chemistry, Ed. K. T. Potts, Pergamon Press Oxford 1984, Vol. 5, pp. 466, 467).

Bases suitable for the cyclisation r₂ are those of which the base strength is sufficient to deprotonate the starting compound of the formula IV. It is possible, however, to use equimolar or less than equimolar (catalytic) amounts of bases.

Bases suitable for the reaction are: alkali metal and alkaline earth metal alcoholates, such as, for example, potassium or sodium methoxide, ethoxide or tert.-butoxide; inorganic bases, such as NaOH, KOH, sodium carbonate etc.; alkali metal and alkaline earth metal hydrides, such as sodium hydride; alkali metal amides, such as sodium amide; nitrogen-containing organic bases, such as DABCO (diazabicyclooctane) etc..

Advantageously, the reaction can also be carried out under phase transfer conditions in a two-phase system. Suitable systems of bases, solvents and phase transfer catalysts are known in the literature.

The cyclisation r₂ can be carried out at temperatures of from 0° C. to the boiling temperature of the reaction mixture, but preferably at temperatures of approximately from 50° to 150° C.

The aminoimidazole V can be isolated and purified according to customary methods by precipitation, crystallisation, extraction or by chromatographic or distillative methods.

In process steps r₃ and r₄, the 4-aminoimidazole of the formula V is reduced to form the desired end product.

For this purpose, compound V is first diazotised according to processes known per se. Diazotisations of heterocyclic amines are generally known (R. N. Butler, Chem. Rev. 75 (1975) 241).

In general, any agent suitable for the diazotisation of aromatic amines is suitable as a diazotisation agent for amines of the formula II.

As suitable agents for diazotisation there may be mentioned: nitrite salts in combination with acids; NO⊕ BF₄⊖; and alkyl nitrites of the formula XII

Alk—O—NO                                              (XIII)

in which Alk represents C₁–C₈-alkyl, especially isoamyl nitrite and tert.-butyl nitrite.

The system nitrite salt/acid is preferred. Especially suitable nitrite salts are sodium nitrite and potassium nitrite.

Suitable acids are mineral acids; organic acids, and a combination of mineral acids with organic acids.

Inter alia the following mineral acids are suitable: hydrohalic acids, such as hydrofluoric acid, hydrochloric acid, hydrobromic acid or hydriodic acid; perhalic acids, such as perchloric acid, perbromic and periodic acid; phosphoric acid; hypophosphorous acid; sulphuric acid, nitric acid; tetrafluoroboric acid, etc..

Organic acids are, for example, trifluoroacetic acid, formic acid, acetic acid, propionic acid, benzene- or toluene-sulphonic acid, sulphonic acids, such as methanesulphonic acid etc..

The mineral acids and organic acids mentioned above can be used in aqueous solution or in the form of a mixture of mineral acid and organic acid, if desired also with the addition of water or co-solvent.

Through suitable selection of the acid and of the nitrite salt and, if desired, of the solvent, the reaction according to the invention can be carried out as a two-stage process, that is to say with isolation of the diazonium salt of the formula VI, or as a one-stage process, that is to say without isolation of the diazonium salt VI.

If it is desirable to isolate the diazonium salt VI, the operation must be carried out at low temperatures and, preferably, using the following mineral acids: hydrochloric acid, perchloric acid, tetrafluoroboric acid, perbromic acid, periodic acid, hexafluorophosphoric acid.

In addition, preferably the operation can be carried out using NO⊕F₄⊖ or isoamyl nitrite/perchlorate or HBF₄.

Generally, however, the diazonium salt of the formula VI can also be produced from the respective aminoimidazoles and the above-mentioned diazotisation agents by carrying out the operation at temperatures of below 0° C.

The reduction of diazonium salts is known in the literature (Organ. Reactions 2, (1944), 262; Org. Synth. Coll. Vol. 3 (1955) 295; Org. Synth. Coll. Vol. 4 (1963) 947; Angew. Chem. 70 (1958) 211; J. Org. Chem. 28 (1963) 568; J. Amer. Chem. Soc. 83 (1961) 1251; Tetrahedron 26 (1970) 4609; J. Org. Chem. 36 (1971) 1725; Chem. Lett. 1979 1051).

Inter alia the following may be mentioned as suitable reducing agents: hypophosphorous acid (H₃PO₂); alcohols, such as methanol, ethanol, n-propanol, isopropanol, butanol; hydrazine; hydrides, such as (C₄H₉)₃—SnH, NaBH₄ complexes, such as RhCl[P(C₆H₃)₃]₃; thiophenol; dioxan; tetrahydrofuran; dimethylformamide or formaldehyde derivatives, especially under alkaline conditions.

A compilation of suitable reducing agents is given in the above-mentioned literature reference "Organic Reactions", to which reference is expressly made.

It is often advantageous if the diazonium salt VI is not isolated but is reduced in situ to form the desired product I. In these cases it has proved advantageous to carry out the diazotisation with NaNO₂/mineral acid optionally with the addition of glacial acetic acid and/or propionic acid and, after the diazotisation, to add hypophosphorous acid directly to the reaction mixture or to carry out the diazotisation reaction in the presence of one of the above-mentioned reducing agents as co-solvent.

The deamination of the aminoimidazoles V can also be carried out preferably by reaction with alkyl nitrites of the formula XIII

Alk—O—NO                                              (XIII), in which Alk represents a C₄–C₈-alkyl radical, the diazotisation preferably, in the manner of a one-stage reaction without isolation of the diazonium salt VI (A⊖ is Alk-O⊖), resulting directly in the end product I with nitrogen being removed. The diazotisation of V with XIII is advantageously carried out in a solvent that is capable of reducing the diazonium salt formed as intermediate, such as dimethylformamide, dioxan, tetrahydrofuran or $C_1$-$C_8$-alcohols (J. C. S. Perkin I, 1973, 541; J. Org. Chem. 42 (1977) 3494 and the above-mentioned literature references).

In an especially advantageous manner, the compounds of the formula I can be prepared in a "one-pot reaction", that is to say without isolation of the intermediates II, IV and V, starting from amines of the formula VIII in accordance with the following scheme:

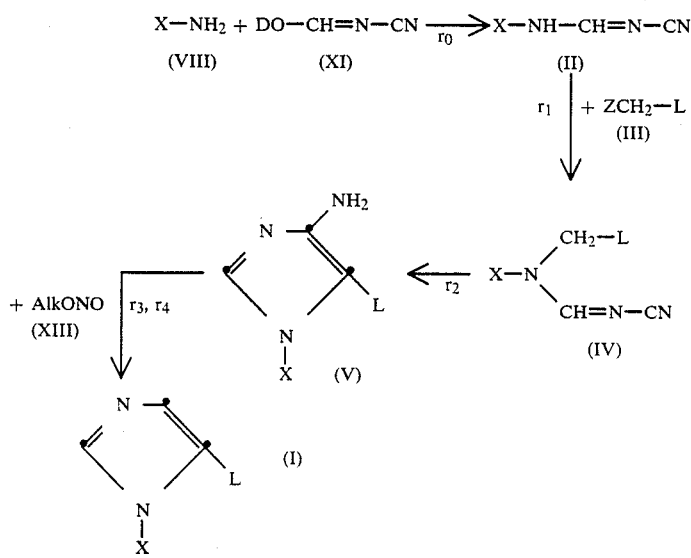

The above-described reaction is preferably carried out in a solvent or a solvent mixture which contains a solvent (or co-solvent) suitable for the reductive diazotisation, such as, for example, dimethylformamide.

The expression "solvents that are inert in the reaction", which is used in the description of the processes $r_1$, $r_2$, $r_3$ and $r_4$, is intended to mean solvents in which the educts or the reaction intermediates can be dissolved, emulsified or suspended without the solvent itself reacting with the educt, the intermediate or with the product, but protolysis reactions are not excluded by this expression.

Suitable solvents are: alcohols, such as methanol, ethanol, propanol, isopropanol, butanol, ethylene glycol etc., ethers, such as diethyl ether, tetrahydrofuran, furan, ethylene glycol mono- or di-methyl or -ethyl ether, diglyme; amides, such as dimethylformamide, N-methylpyrrolidone, dimethylacetamide etc., sulphones and sulphoxides, such as sulfolane, dimethylsulphoxide etc., ketones, such as acetone, methyl ethyl ketone etc., esters, such as ethyl acetate, butyl acetate etc., halogenated hydrocarbons, such as di-, tri- and tetrachloromethane, tetrachloroethylene etc., nitriles, such as acetonitrile, propionitrile; isocyclic and acyclic hydrocarbons, such as petroleum, benzene, toluene, xylene, chlorobenzene, nitrobenzene, pentane, hexane, heptane etc.; and also water and optionally aqueous bases or acids.

In the case of the diazotisation ($r_3$) and the reduction ($r_4$), aqueous systems of mineral acids and organic acids are also suitable.

The following Examples illustrate the invention:

PREPARATION EXAMPLE 1: AMINOMETHYLENECYANAMIDES OF THE FORMULA II

Example 1.01:
N-(2,2-dimethyl-1,2,3,4-tetrahydronaphth-1-yl)-aminomethylenecyanamide 19.3 g (0.11 mol) of 1-amino-2,2-dimethyl-1,2,3,4-tetrahydronaphthalene are placed in 50 ml of absolute ethanol and 10.8 g (0.11 mol) of ethoxymethylenecyanamide are added. The solution is stirred for 90 minutes under reflux and then concentrated. The initially oily residue crystallises on trituration.

16.3 g (65% of the theoretical yield) of the title compound of the formula

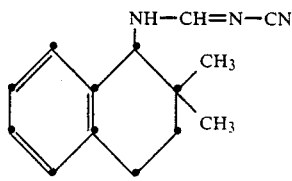

are isolated in the form of colourless crystals having a melting point of 140°–142° C. (Comp. No. 1.01).

Example 1.02:
N-(2,2-dimethylindan-1-yl)-aminomethylenecyanamide

The title compound of the formula

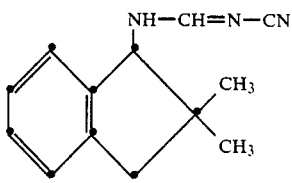

is obtained in a 96% yield in the form of colourless crystals having a melting point of 164°–167° C. (Comp. No. 1.02) analogously to Example 1.01 starting from 1-amino-2,2-dimethylindane and ethoxymethylenecyanamide.

Example 1.03:
N-(2,6-dimethylphenyl)-aminomethylenecyanamide

The title compound of the formula

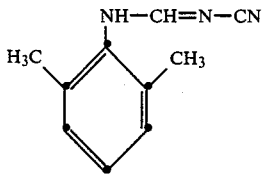

is obtained in a 56% yield in the form of colourless crystals having a melting point of 162°-165° C. (Comp. No. 1.03) analogously to Example 1.01 starting from 2,6-dimethylaniline and ethoxymethylenecyanamide.

Example 1.04:
N-(diphenylmethyl)-aminomethylenecyanamide

The title compound of the formula

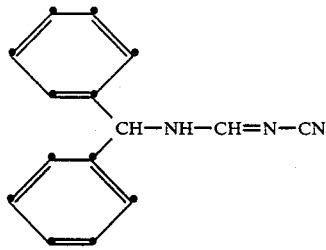

is obtained in an 83% yield in the form of colourless crystals having a melting point of 158°-160° C. (Comp. No. 1.04) analogously to Example 1.01 starting from diphenylmethylamine and ethoxymethylenecyanamide.

Example 1.05:
(+)-N-(2,2-dimethylindan-1-yl)-aminomethylenecyanamide 54.7 g (92%) of the title compound of the formula

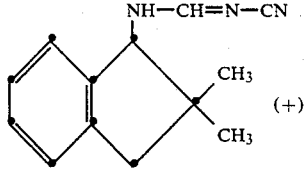

$[\alpha]_D^{20}$: +144.0±3° (CHCl$_3$), m.p. 164°-167° C. (Comp. No. 1.123), are obtained analogously to Example 1.01 from 45.2 g of (−)-1-amino-2,2-dimethylindane (ee~90%) and 27.5 g of ethoxymethylenecyanamide in 60 ml of ethanol.

The compounds of Table 1 can be obtained analogously to the above Examples.

TABLE 1

| Comp. No. | Compounds of the formula X—NH—CH=N—CN X | phys. data |
|---|---|---|
| 1.01 | 2,2-Dimethyl-1,2,3,4-tetrahydronaphthalen-1-yl | M.p. 140-142° C. |
| 1.02 | 2,2-Dimethyl-indan-1-yl | M.p. 164-167° C. |
| 1.03 | 2,6-Dimethylphenyl | M.p. 162-165° C. |
| 1.04 | Diphenylmethyl | M.p. 158-160° C. |
| 1.05 | Indan-1-yl | |
| 1.06 | 2-Methyl-indan-1-yl | |
| 1.07 | cis-2-Methyl-indan-1-yl | |
| 1.08 | trans-2-Methyl-indan-1-yl | |
| 1.09 | 1,2,3,4-Tetrahydronaphthalen-1-yl | |
| 1.10 | 2-Methyl-1,2,3,4-tetrahydronaphthalen-1-yl | |
| 1.11 | cis-2-Methyl-1,2,3,4-tetrahydronaphthalen-1-yl | |
| 1.12 | trans-2-Methyl-1,2,3,4-tetrahydro-naphthalen-1-yl | |
| 1.13 | Benzocycloheptan-5-yl | |
| 1.14 | 4,5,6,7-Tetrahydrobenzo[b]thiophen-4-yl | |
| 1.15 | 4,5,6,7-Tetrahydrobenzo[b]furan-4-yl | |
| 1.16 | 5,6,7,8-Tetrahydroquinolin-5-yl | |
| 1.17 | 5,6,7,8-Tetrahydroisoquinolin-5-yl | |
| 1.18 | 5,6,7,8-Tetrahydroquinolin-8-yl | |
| 1.19 | 5,6,7,8-Tetrahydroisoquinolin-8-yl | |
| 1.20 | 9,10-Dihydroanthracen-9-yl | |
| 1.21 | 9H-Fluoren-9-yl | |
| 1.22 | Dibenzo[a,d]cycloheptan-5-yl | |
| 1.23 | Dibenzo[a,d]cycloheptan-5-yl | |
| 1.24 | 1,2-Dihydronaphthalin-1-yl | |
| 1.25 | (4-Chlorophenyl)-(phenyl)-methyl | |
| 1.26 | 2-Ethyl-6-methyl-phenyl | oil |
| 1.27 | 2,6-Diethyl-phenyl | oil |
| 1.28 | 2,6-Di-isopropyl-phenyl | M.p. 131-135° C. |
| 1.29 | 2,4,6-Trimethyl-phenyl | |
| 1.30 | 4-Chloro-2,6-dimethyl-phenyl | |
| 1.31 | 2-Ethyl-indan-1-yl | |
| 1.32 | cis-2-Ethyl-indan-1-yl | |
| 1.33 | trans-2-Ethyl-indan-1-yl | |
| 1.34 | 2-Propyl-indan-1-yl | |
| 1.35 | cis-Propyl-indan-1-yl | |
| 1.36 | trans-Propyl-indan-1-yl | |
| 1.37 | 2-Isopropyl-indan-1-yl | |
| 1.38 | 2-Ethyl-2-methyl-indan-1-yl | |
| 1.39 | 2-Methyl-2-propyl-indan-1-yl | |
| 1.40 | 2,2-Diethyl-indan-1-yl | |
| 1.41 | 2,2-Dipropyl-indan-1-yl | |
| 1.42 | Spiro-[cyclopropane-1,2'-indan]-1'-yl | |
| 1.43 | Spiro-[cyclopentane-1,2'-indan]-1'-yl | |
| 1.44 | Spiro-[cyclohexane-1,2'-indan]-1'-yl | |
| 1.45 | 2-Ethyl-1,2,3,4-tetrahydronaphthalen-1-yl | |
| 1.46 | cis-2-Ethyl-1,2,3,4-tetrahydronaphthalen-1-yl | |
| 1.47 | trans-2-Ethyl-1,2,3,4-tetrahydronaphthalen-1-yl | |
| 1.48 | 2-Propyl-1,2,3,4-tetrahydronaphthalen-1-yl | |
| 1.49 | cis-2-Propyl-1,2,3,4-tetrahydronaphthalen-1-yl | |
| 1.50 | trans-2-Propyl-1,2,3,4-tetrahydronaphthalen-1-yl | |
| 1.51 | 2-Ethyl-2-methyl-1,2,3,4-tetrahydronaphthalen-1-yl | |
| 1.52 | 2-Methyl-2-propyl-1,2,3,4-tetrahydronaphthalen-1-yl | |
| 1.53 | 2,2-Diethyl-1,2,3,4-tetrahydronaphthalen-1-yl | |
| 1.54 | 2,2-Dipropyl-1,2,3,4-tetrahydronaphthalen-1-yl | |

TABLE 1-continued

Compounds of the formula
X—NH—CH=N—CN

| Comp. No. | X | phys. data |
|---|---|---|
| 1.55 | Spiro[cyclopropane-1,2'-(1',2',3',4'-tetrahydro-naphthalen)]-1'-yl | |
| 1.56 | Spiro[cyclopentane-1,2'-(1',2',3',4'-tetrahydro-naphthalin)]-1'-yl | |
| 1.57 | Spiro[cyclohexane-1,2'-(1',2',3',4'-tetrahydro-naphthalen)]-1'-yl | |
| 1.58 | Chroman-4-yl | |
| 1.59 | 3-Methylchroman-4-yl | |
| 1.60 | cis-3-Methylchroman-4-yl | |
| 1.61 | trans-3-Methylchroman-4-yl | |
| 1.62 | 3-Ethylchroman-4-yl | |
| 1.63 | cis-3-Ethylchroman-4-yl | |
| 1.64 | trans-3-Ethylchroman-4-yl | |
| 1.65 | 3-Propylchroman-4-yl | |
| 1.66 | cis-3-Propylchroman-4-yl | |
| 1.67 | trans-3-Propylchroman-4-yl | |
| 1.68 | 3-Ethyl-3-methyl-chroman-4-yl | |
| 1.69 | 3-Methyl-3-propyl-chroman-4-yl | |
| 1.70 | 3-Isopropylchroman-4-yl | |
| 1.71 | cis 3-Isopropylchroman-4-yl | |
| 1.72 | trans-3-Isopropylchroman-4-yl | |
| 1.73 | 3,3-Dimethylchroman-4-yl | |
| 1.74 | 3,3-Diethylchroman-4-yl | |
| 1.75 | 3,3-Dipropylchroman-4-yl | |
| 1.76 | Spiro[cyclopropane-1,3'-chroman]-4'-yl | |
| 1.77 | Spiro[cyclopentane-1,3'-chroman]-4'-yl | |
| 1.78 | Spiro[cyclohexane-1,3'-chroman]-4'-yl | |
| 1.79 | 2-Methylchroman-4-yl | |
| 1.80 | cis-2-Methylchroman-4-yl | |
| 1.81 | trans-2-Methylchroman-4-yl | |
| 1.82 | 2-Ethylchroman-4-yl | |
| 1.83 | cis-2-Ethylchroman-4-yl | |
| 1.84 | trans-2-Ethylchroman-4-yl | |
| 1.85 | 2-Propylchroamn-4-yl | |
| 1.86 | cis-2-Propylchroman-4-yl | |
| 1.87 | trans-2-Propylchroman-4-yl | |
| 1.88 | 2-Ethyl-2-methylchroman-4-yl | |
| 1.89 | 2-Methyl-2-propylchroman-4-yl | |
| 1.90 | 2-Isopropylchroman-4-yl | |
| 1.91 | cis-2-Isopropylchroman-4-yl | |
| 1.92 | trans-2-Isopropylchroman-4-yl | |
| 1.93 | 2,2-Dimethylchroman-4-yl | |
| 1.94 | 2,2-Diethylchroman-4-yl | |
| 1.95 | 2,2-Dipropylchroman-4-yl | |
| 1.96 | Spiro[cyclopropan-1,2'-chroman]-4'-yl | |
| 1.97 | Spiro[cyclopentane-1,2'-chroman]-4'-yl | |
| 1.98 | Spiro[cyclohexane-1,2'-chroman]-4'-yl | |
| 1.99 | 2,3-Dimethyl-chroman-4-yl | |
| 1.100 | [cis-2,3-Dimethyl]-chroman-4-yl | |
| 1.101 | [trans-2,3-Dimethyl]-chroman-4-yl | |
| 1.102 | Thiochroman-4-yl | |
| 1.103 | 2,2-Dimethylthiochroman-4-yl | |
| 1.104 | 3,3-Dimethylthiochroman-4-yl | |
| 1.105 | 2,3-Dimethylthiochroman-4-yl | |
| 1.106 | [cis-2,3-Dimethyl]thio-chroman-4-yl | |
| 1.107 | [trans-2,3-Dimethyl]thio-chroman-4-yl | |
| 1.108 | 2-Methyl-thiochroman-4-yl | |
| 1.109 | 2-Ethyl-thiochroman-4-yl | |
| 1.110 | 2-Ethyl-2-methyl-thio-chroman-4-yl | |
| 1.111 | 2,2-Diethyl-thiochroman-4-yl | |
| 1.112 | 3,3-Diethyl-thiochroman-4-yl | |
| 1.113 | 3-Ethyl-3-methyl-thio-chroman-4-yl | |
| 1.120 | 2,3-Dimethylindan-1-yl | |
| 1.121 | [cis-2,3-Dimethyl]indan-1-yl | |
| 1.122 | [trans-2,3-Dimethyl]indan-1-yl | |
| 1.123 | (+)-2,2-Dimethylindan-1-yl | M.p. 164–167° C. |
| 1.124 | (−)-2,2-Dimethylindan-1-yl | |
| 1.125 | (+)-2,2-Dimethylindan-1-yl | |
| 1.126 | (−)-2,2-Dimethyl-1,2,3,4-tetrahydronaphthalin-1-yl | |
| 1.127 | (+)-2,2-Dimethyl-1,2,3,4-tetrahydronaphthalin-1-yl | |
| 1.128 | 3,3-Dimethylindan-1-yl | |
| 1.129 | 3-Methylindan-1-yl | |

PREPARATION EXAMPLE 2: CYANAMIDES OF THE FORMULA IV

Example 2.01:
N-(methoxycarbonylmethyl)-N-(2,2-dimethyl-1,2,3,4-tetrahydronaphth-1-yl)-aminomethylene-cyanamide 120.7 g (0.531 mol) of compound 1.01 are suspended in 200 ml of methanol and 95.6 g (0.531 mol) of 30% sodium methoxide/methanol are added. The whole is then stirred at room temperature until everything has dissolved. The majority of the solvent is distilled off and the residue is taken up in 400 ml of DMSO. Then, the remaining methanol is removed by five times adding 300 ml of hexane and subsequently distilling the mixture. While cooling, 92.1 g (0.584 mol) of bromoacetic acid methyl ester are then added dropwise at 20° C. After a short time NaBr is precipitated. The suspension is stirred for 2 hours at 30° and is then diluted with 2 l of water. The oil that separates is taken up in ethyl acetate and dried over $Na_2SO_4$/carbon. The solvent is distilled off, yielding a yellow oil which crystallises when stirred with acetone/ether.

87 g (55%) of the title compound of the formula

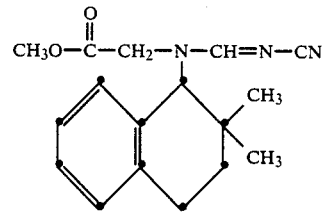

are isolated in the form of colourless crystals having a melting point of 125°–127° C. (Comp. No. 2.01).

Example 2.02:
N-(methoxycarbonylmethyl)-N-(2,2-dimethyl-indan-1-yl)-aminomethylene-cyanamide 32.0 g (0.15 mol) of compound 2.02 are suspended in 160 ml of methanol and 17.3 g (0.15 mol) of K tert.-butoxide are added. The clear solution is concentrated to dryness by evaporation and the K salt that remains is dried by 3 times adding 250 ml of toluene and subsequently distilling the mixture, and then dissolved in 80 ml of DMSO. After the addition of 0.5 g of NaI, 23.6 g (0.15 mol) of bromoacetic acid methyl ester are added dropwise while cooling at 20°–25° C. The mixture is stirred at 90° for 2 hours and, after cooling, is poured into water, and the oil that separates is taken up in ethyl acetate. After drying over Na$_2$SO$_4$/carbon, the solvent is distilled off. The oil that remains crystallises on stirring with a small amount of methanol.

19.3 g (46%) of the title compound of the formula

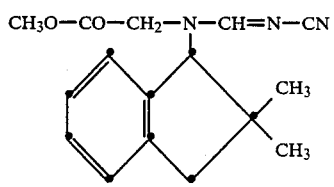

are isolated in the form of colourless cyrstals having a melting point of 120°–123° C. (Comp. No. 2.02).

Example 2.03:
N-(methoxycarbonylmethyl)-N-(2,6-dimethylphenyl)aminomethylene-cyanamide 17.3 g (0.1 mol) of compound No. 1.03, 10.8 g (0.1 mol) of sodium carbonate, 15.8 g (0.1 mol) of bromoacetic acid methyl ester, 0.5 g of NaI and 0.5 g of 18-Crown-6 in 100 ml of DMSO are stirred for 5 hours at room temperature and then for 2 hours at 100°. After cooling, the whole is stirred into 1 l of water and adjusted to pH 6 with acetic acid (CO$_2$ ↑). The product is precipitated in the form of crystals.

16.0 g (65%) of the title compound of the formula

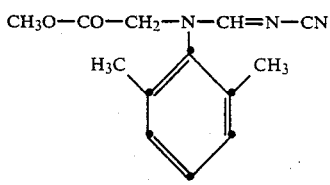

are isolated in the form of crystals having a melting point of 153°–156° C. (Comp. No. 2.03).

Example 2.04:
N-(methoxycarbonylmethyl)-N-(diphenylmethyl)-aminomethylenecyanamide 17.3 g (0.073 mol) of compound No. 1.04 are dissolved in 100 ml of DMSO and 9.0 g (0.078 mol) of K tert.-butoxide are added. The clear red solution is stirred at room temperature for 1 hour and then 12.3 g (0.078 mol) of bromoacetic acid methyl ester are added dropwise, the solution turning yellow. The whole is stirred at room temperature for a further 2 hours and is then diluted with water.

The oil that separates is taken up in ethyl acetate and dried over Na$_2$SO$_4$/carbon. After distilling off the solvent, the product remains behind in the form of a yellow oil.

17.1 g (76%) of the title compound of the formula

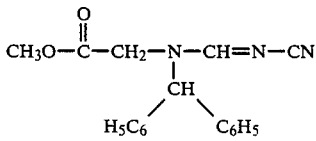

are isolated in the form of a yellow oil (Comp. No. 2.04), which crystallises after standing for a relatively long period (m.p. 108°–110° C.).

Example 2.05:
(+)-N-(2,2-dimethylindan-1-yl)-N-(methoxycarbonylmethyl)-aminomethylenecyanamide Analogously to Example 2.04, starting from 50.3 g of (+)-N-(2,2-dimethylindan-1-yl)-aminomethylenecyanamide, 26.5 g of K tert.-butoxide and 36.1 g of bromoacetic acid methyl ester in 100 ml of dimethyl sulphoxide, 34.8 g (52%) of the title compound of the formula

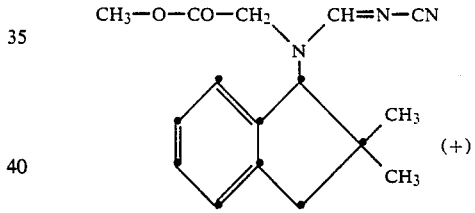

are obtained in the form of crystals having a melting point of 116°–119° C. and an optical rotation $[\alpha]_D^{20}$ of +75.1±0.4 (CHCl$_3$) (Comp. No. 2.143).

The compounds of Table 2 can be obtained analogously to the above Examples 2.01 to 2.05.

TABLE 2

Compounds of the formula

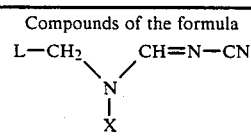

| Comp. No. | X | L | phys. data |
|---|---|---|---|
| 2.01 | 2,2-Dimethyl-1,2,3,4-tetrahydronaphthalen-1-yl | COOCH$_3$ | M.p. 125–127° C. |
| 2.02 | 2,2-Dimethyl-indan-1-yl | COOCH$_3$ | M.p. 120–123° C. |
| 2.03 | 2,6-Dimethylphenyl | COOCH$_3$ | M.p. 153–156° C. |
| 2.04 | Diphenylmethyl | COOCH$_3$ | M.p. 108–110° C. |
| 2.05 | Indan-1-yl | COOCH$_3$ | |
| 2.06 | 2-Methyl-indan-1-yl | COOCH$_3$ | |
| 2.07 | cis-2-Methyl-indan-1-yl | COOCH$_3$ | |
| 2.08 | trans-2-Methyl-indan-1-yl | COOCH$_3$ | |
| 2.09 | 1,2,3,4-Tetrahydronaphtha- | COOCH$_3$ | |

TABLE 2-continued

Compounds of the formula $$L-CH_2\underset{\underset{X}{\overset{|}{N}}}{\diagdown}CH=N-CN$$

| Comp. No. | X | L | phys. data |
|---|---|---|---|
| | len-1-yl | | |
| 2.10 | 2-Methyl-1,2,3,4-tetrahydro-naphthalen-1-yl | COOCH$_3$ | |
| 2.11 | cis-2-Methyl-1,2,3,4-tetra-hydronaphthalen-1-yl | COOCH$_3$ | |
| 2.12 | trans-2-Methyl-1,2,3,4-tetrahydro-naphthalen-1-yl | COOCH$_3$ | |
| 2.13 | Benzocycloheptan-5-yl | COOCH$_3$ | |
| 2.14 | 4,5,6,7-Tetrahydrobenzo[b]-thiophen-4-yl | COOCH$_3$ | |
| 2.15 | 4,5,6,7-Tetrahydrobenzo[b]-furan-4-yl | COOCH$_3$ | |
| 2.16 | 5,6,7,8-Tetrahydroquinolin-5-yl | COOCH$_3$ | |
| 2.17 | 5,6,7,8-Tetrahydroiso-quinolin-5-yl | COOCH$_3$ | |
| 2.18 | 5,6,7,8-Tetrahydroquinolin-8-yl | COOCH$_3$ | |
| 2.19 | 5,6,7,8-Tetrahydroiso-quinolin-8-yl | COOCH$_3$ | |
| 2.20 | 9,10-Dihydroanthracen-9-yl | COOCH$_3$ | |
| 2.21 | 9H-Fluoren-9-yl | COOCH$_3$ | |
| 2.22 | Dibenzo[a,d]cyclohepten-5-yl | COOCH$_3$ | |
| 2.23 | Dibenzo[a,d]cycloheptan-5-yl | COOCH$_3$ | |
| 2.24 | 1,2-Dihydronaphthalen-1-yl | COOCH$_3$ | |
| 2.25 | (4-Chlorophenyl)-(phenyl)-methyl | COOCH$_3$ | |
| 2.26 | 2-Ethyl-6-methyl-phenyl | COOCH$_3$ | M.p. 113–116° C. |
| 2.27 | 2,6-Diethyl-phenyl | COOCH$_3$ | oil |
| 2.28 | 2,6-Di-isopropyl-phenyl | COOCH$_3$ | M.p. 141–143° C. |
| 2.29 | 2,4,6-Trimethyl-phenyl | COOCH$_3$ | |
| 2.30 | 4-Chloro-2,6-dimethyl-phenyl | COOCH$_3$ | |
| 2.31 | 2-Ethyl-indan-1-yl | COOCH$_3$ | |
| 2.32 | cis-2-Ethyl-indan-1-yl | COOCH$_3$ | |
| 2.33 | trans-2-Ethyl-indan-1-yl | COOCH$_3$ | |
| 2.34 | 2-Propyl-indan-1-yl | COOCH$_3$ | |
| 2.35 | cis-Propyl-indan-1-yl | COOCH$_3$ | |
| 2.36 | trans-Propyl-indan-1-yl | COOCH$_3$ | |
| 2.37 | 2-Isopropyl-indan-1-yl | COOCH$_3$ | |
| 2.38 | 2-Ethyl-2-methyl-indan-1-yl | COOCH$_3$ | |
| 2.39 | 2-Methyl-2-propyl-indan-1-yl | COOCH$_3$ | |
| 2.40 | 2,2-Diethyl-indan-1-yl | COOCH$_3$ | |
| 2.41 | 2,2-Dipropyl-indan-1-yl | COOCH$_3$ | |
| 2.42 | Spiro-[cyclopropane-1,2'-indan]-1'-yl | COOCH$_3$ | |
| 2.43 | Spiro-[cyclopentane-1,2'-indan]-1'-yl | COOCH$_3$ | |
| 2.44 | Spiro-[cyclohexane-1,2'-indan]-1'-yl | COOCH$_3$ | |
| 2.45 | 2-Ethyl-1,2,3,4-tetrahydro-naphthalen-1-yl | COOCH$_3$ | |
| 2.46 | cis-2-Ethyl-1,2,3,4-tetra-hydronaphthalen-1-yl | COOCH$_3$ | |
| 2.47 | trans-2-Ethyl-1,2,3,4-tetra-hydronaphthalen-1-yl | COOCH$_3$ | |
| 2.48 | 2-Propyl-1,2,3,4-tetra-hydronaphthalen-1-yl | COOCH$_3$ | |
| 2.49 | cis-2-Propyl-1,2,3,4-tetra-hydronaphthalen-1-yl | COOCH$_3$ | |
| 2.50 | trans-2-Propyl-1,2,3,4-tetrahydronaphthalen-1-yl | COOCH$_3$ | |
| 2.51 | 2-Ethyl-2-methyl-1,2,3,4-tetrahydronaphthalen-1-yl | COOCH$_3$ | |
| 2.52 | 2-Methyl-2-propyl-1,2,3,4-tetrahydronaphthalen-1-yl | COOCH$_3$ | |
| 2.53 | 2,2-Diethyl-1,2,3,4-tetra-hydronaphthalen-1-yl | COOCH$_3$ | |
| 2.54 | 2,2-Dipropyl-1,2,3,4-tetra-hydronaphthalen-1-yl | COOCH$_3$ | |
| 2.55 | Spiro[cyclopropane-1,2'-(1',2',3', 4'-tetrahydro-naphthalen)]-1'-yl | COOCH$_3$ | |
| 2.56 | Spiro[cyclopentane-1,2'- | COOCH$_3$ | |

TABLE 2-continued

Compounds of the formula

L—CH₂  CH=N—CN
     \ /
      N
      |
      X

| Comp. No. | X | L | phys. data |
|---|---|---|---|
| 2.57 | Spiro[cyclohexan-1,2'-(1',2',3',4',-tetrahydro-naphthalen)]-1'-yl (1',2',3', 4'-tetrahydro-naphthalen)]-1'-yl | COOCH₃ | |
| 2.58 | Chroman-4-yl | COOCH₃ | |
| 2.59 | 3-Methylchroman-4-yl | COOCH₃ | |
| 2.60 | cis-3-Methylchroman-4-yl | COOCH₃ | |
| 2.61 | trans-3-Methylchroman-4-yl | COOCH₃ | |
| 2.62 | 3-Ethylchroman-4-yl | COOCH₃ | |
| 2.63 | cis-3-Ethylchroman-4-yl | COOCH₃ | |
| 2.64 | trans-3-Ethylchroman-4-yl | COOCH₃ | |
| 2.65 | 3-Propylchroman-4-yl | COOCH₃ | |
| 2.66 | cis-3-Propylchroman-4-yl | COOCH₃ | |
| 2.67 | trans-3-Propylchroman-4-yl | COOCH₃ | |
| 2.68 | 3-Ethyl-3-methyl-chroman-4-yl | COOCH₃ | |
| 2.69 | 3-Methyl-3-propyl-chroman-4-yl | COOCH₃ | |
| 2.70 | 3-Isopropylchroman-4-yl | COOCH₃ | |
| 2.71 | cis 3-Isopropylchroman-4-yl | COOCH₃ | |
| 2.72 | trans-3-Isopropylchroman-4-yl | COOCH₃ | |
| 2.73 | 3,3-Dimethylchroman-4-yl | COOCH₃ | |
| 2.74 | 3,3-Diethylchroman-4-yl | COOCH₃ | |
| 2.75 | 3,3-Dipropylchroman-4-yl | COOCH₃ | |
| 2.76 | Spiro[cyclopropane-1,3'-chroman]-4'-yl | COOCH₃ | |
| 2.77 | Spiro[cyclopentane-1,3'-chroman]-4'-yl | COOCH₃ | |
| 2.78 | Spiro[cyclohexane-1,3'-chroman]-4'-yl | COOCH₃ | |
| 2.79 | 2,2-Dimethylindan-1-yl | COOC₂H₅ | |
| 2.80 | 2,2-Dimethylindan-1-yl | COO-i-C₃H₇ | |
| 2.81 | 2,2-Dimethylindan-1-yl | COO—CH₂—CH=CH₂ | |
| 2.82 | 2,2-Dimethylindan-1-yl | COO—cyclopropyl | |
| 2.83 | 2,2-Dimethylindan-1-yl | CO—NH CH₃ | |
| 2.84 | 2,2-Dimethylindan-1-yl | CO—N(CH₃)₂ | |
| 2.85 | 2,2-Dimethylindan-1-yl | CN | |
| 2.86 | 2,2-Dimethyl-1,2,3,4-tetra-hydronaphthalen-1-yl | COOC₂H₅ | |
| 2.87 | 2,2-Dimethyl-1,2,3,4-tetra hydronaphthalen-1-yl | COO-i-C₃H₇ | |
| 2.88 | 2,2-Dimethyl-1,2,3,4-tetra hydronaphthalen-1-yl | COO—CH₂—CH=CH₂ | |
| 2.89 | 2,2-Dimethyl-1,2,3,4-tetra-hydronaphthalen-1-yl | COO—cyclopropyl | |
| 2.90 | 2,2-Dimethyl-1,2,3,4-tetra-hydronaphthalen-1-yl | CO—NH CH₃ | |
| 2.91 | 2,2-Dimethyl-1,2,3,4-tetra-hydronaphthalen-1-yl | CO—N(CH₃)₂ | |
| 2.92 | 2,2-Dimethyl-1,2,3,4-tetra-hydronaphthalen-1-yl | CN | |
| 2.93 | 2,6-Dimethylphenyl | COOC₂H₅ | |
| 2.94 | 2,6-Dimethylphenyl | COO-i-C₃H₇ | |
| 2.95 | 2,6-Dimethylphenyl | COO—CH₂—CH=CH₂ | |
| 2.96 | 2,6-Dimethylphenyl | COO—cyclopropyl | |

TABLE 2-continued

Compounds of the formula

L—CH$_2$\\_N_/CH=N—CN
|
X

| Comp. No. | X | L | phys. data |
|---|---|---|---|
| 2.97 | 2,6-Dimethylphenyl | CO—NH CH$_3$ | |
| 2.98 | 2,6-Dimethylphenyl | CO—N(CH$_3$)$_2$ | |
| 2.99 | 2,6-Dimethylphenyl | CN | |
| 2.100 | Diphenylmethyl | COOC$_2$H$_5$ | |
| 2.101 | Diphenylmethyl | COO-i-C$_3$H$_7$ | |
| 2.102 | Diphenylmethyl | COO—CH$_2$—CH=CH$_2$ | |
| 2.103 | Diphenylmethyl | 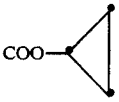 | |
| 2.104 | Diphenylmethyl | CO—NH CH$_3$ | |
| 2.105 | Diphenylmethyl | CO—N(CH$_3$)$_2$ | |
| 2.106 | Diphenylmethyl | CN | |
| 2.107 | 2-Methylchroman-4-yl | COOCH$_3$ | |
| 2.108 | cis-2-Methylchroman-4-yl | COOCH$_3$ | |
| 2.109 | trans-2-Methylchroman-4-yl | COOCH$_3$ | |
| 2.110 | 2-Ethylchroman-4-yl | COOCH$_3$ | |
| 2.111 | cis-2-Ethylchroman-4-yl | COOCH$_3$ | |
| 2.112 | trans-2-Ethylchroman-4-yl | COOCH$_3$ | |
| 2,113 | 2-Propylchroman-4-yl | COOCH$_3$ | |
| 2.114 | cis-2-Propylchroman-4-yl | COOCH$_3$ | |
| 2.115 | trans-2-Propylchroman-4-yl | COOCH$_3$ | |
| 2.116 | 2-Ethyl-2-methyl-chroman-4-yl | COOCH$_3$ | |
| 2.117 | 2-Methyl-2-propyl-chroman-4-yl | COOCH$_3$ | |
| 2.118 | 2-Isopropylchroman-4-yl | COOCH$_3$ | |
| 2.119 | cis 2-Isopropylchroman-4-yl | COOCH$_3$ | |
| 2.120 | trans-2-Isopropylchroman-4-yl | COOCH$_3$ | |
| 2.121 | 2,2-Dimethylchroman-4-yl | COOCH$_3$ | |
| 2.122 | 2,2-Diethylchroman-4-yl | COOCH$_3$ | |
| 2.123 | 2,2-Dipropylchroman-4-yl | COOCH$_3$ | |
| 2.124 | Spiro[cyclopropane-1,2'-chroman]-4'-yl | COOCH$_3$ | |
| 2.125 | Spiro[cyclopentane-1,2'-chroman]-4'-yl | COOCH$_3$ | |
| 2.126 | Spiro[cyclohexane-1,2'-chroman]-4'-yl | COOCH$_3$ | |
| 2.127 | 2,2-Dimethyl-1,2,3,4-tetrahydronaphthalen-1-yl | CO—NH-i-C$_3$H$_7$ | |
| 2.128 | Thiochroman-4-yl | COOCH$_3$ | |
| 2.129 | 2,2-Dimethylthiochroman-4-yl | COOCH$_3$ | |
| 2.130 | 3,3-Dimethylthiochroman-4-yl | COOCH$_3$ | |
| 2.131 | 2,3-Dimethylthiochroman-4-yl | COOCH$_3$ | |
| 2.132 | [cis-2,3-Dimethyl]thiochroman-4-yl | COOCH$_3$ | |
| 2.133 | [trans-2,3-Dimethyl]thiochroman-4-yl | COOCH$_3$ | |
| 2.134 | 2-Methyl-thiochroman-4-yl | COOCH$_3$ | |
| 2.135 | 2-Ethyl-thiochroman-4-yl | COOCH$_3$ | |
| 2.136 | 2-Methyl-2-ethyl-thiochroman-4-yl | COOCH$_3$ | |
| 2.137 | 2,2-Diethyl-thiochroman-4-yl | COOCH$_3$ | |
| 2.138 | 3,3-Diethyl-thiochroman-4-yl | COOCH$_3$ | |
| 2.139 | 3-Methyl-3-ethyl-thio chroman-4-yl | COOCH$_3$ | |
| 2.140 | 2,3-Dimethylindan-1-yl | COOCH$_3$ | |
| 2.141 | [cis-2,3-Dimethyl]indan-1-yl | COOCH$_3$ | |
| 2.142 | [trans-2,3-Dimethyl]indan-1-yl | COOCH$_3$ | |
| 2.143 | (+)-2,2-Dimethylindan-1-yl | COOCH$_3$ | M.p. 116-119° C. |
| 2.144 | (−)-2,2-Dimethylindan-1-yl | COOCH$_3$ | |
| 2.145 | (+)-2,2-Dimethyl-1,2,3,4-tetrahydronaphthalen-1-yl | COOCH$_3$ | |
| 2.146 | (−)-2,2-Dimethyl-1,2,3,4-tetrahydronaphthalen-1-yl | COOCH$_3$ | |
| 2.147 | 2,2-Dimethyl-1,2,3,4-tetra- | CONH—C$_3$H$_7$(i) | M.p. 186-188° C. |

TABLE 2-continued

Compounds of the formula

L—CH$_2$—N(X)—CH=N—CN

| Comp. No. | X | L | phys. data |
|---|---|---|---|
| | hydronaphthalen-1-yl | | |

PREPARATION EXAMPLE 3:
4-AMINOIMIDAZOLES OF THE FORMULA V

Example 3.01:
4-amino-1-(2,2-dimethyl-1,2,3,4-tetra-hydronaphth-1-yl)-imidazole-5-carboxylic acid methyl ester 10.0 g of compound 2.01 are suspended in 30 ml of methanol and, after the addition of 1.0 g (0.006 mol) of 30% Na methoxide/methanol, the whole is heated at the boil for 2 hours. After the resulting solution has cooled it is diluted with water. The product crystallises.

8.4 g (84%) of the title compound of the formula

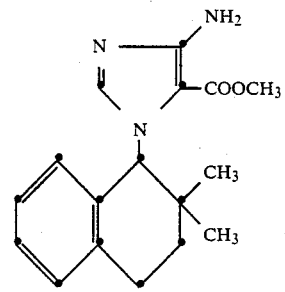

are isolated in the form of colourless crystals having a melting point of 193°-195° C. (Comp. No. 3.01).

Example 3.02:
4-amino-1-(2,2-dimethyl-indan-1-yl)-imidazole-5-carboxylic acid methyl ester 12.2 g (0.043 mol) of compound 2.02 are suspended in 30 ml of methanol and, after the addition of 1.6 g (0.009 mol) of 30% Na methoxide/methanol, the whole is stirred at reflux for 1 hour. After cooling, the resulting solution is diluted with water and adjusted to pH 7 with acetic acid. The crystalline product is filtered and dried.

11.8 g (98%) of the title compound of the formula

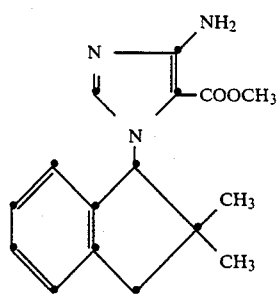

are isolated in the form of colourless crystals having a melting point of 167°-168° C. (Comp. No. 3.02).

Example 3.03:
4-amino-1-(2,6-dimethyl-phenyl)-imidazole-5-carboxylic acid methyl ester 2.5 g (0.01 mol) of compound No. 2.03 are suspended in 30 ml of methanol and, after the addition of 0.2 g (0.001 mol) of 30% Na methoxide/methanol, the whole is stirred for 1 hour at 60° C. After the resulting clear solution has cooled it is diluted with water. The product crystallises.

2.1 g (88%) of the title compound of the formula

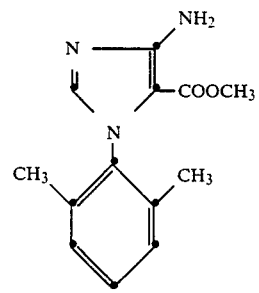

are isolated in the form of colourless crystals having a melting point of 154°-156° C. (Comp. No. 3.03).

Example 3.04:
4-amino-1-(diphenylmethyl)-imidazole-5-carboxylic acid methyl ester 15.2 g (0.049 mol) of compound No. 2.04 are dissolved in 50 ml of methanol. After the addition of 0.45 g (0.002 mol) of 30% sodium ethoxide/methanol, the whole is stirred for 1 hour at 60°, during which time the product is precipitated in the form of crystals. After cooling, the product is diluted with water and cooled.

12.5 g (83%) of the title compound of the formula

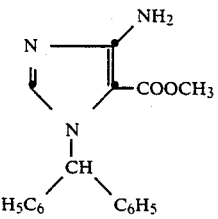

are isolated in the form of colourless crystals having a melting point of 199°-201° C. (Comp. No. 3.04).

Example 3.05: Process for the preparation of 4-aminoimidazoles of the formula V from amines of the formula VIII, without isolation of the intermediates: 4-amino-1-(2,2-dimethylindan-1-yl)-imidazole-5-carboxylic acid methyl ester 3.9 g of ethoxymethylenecyanamide are added to a solution of 6.4 g of 1-amino-2,2-dimethylindane in 50 ml of dimethylformamide. The temperature rises to 40° C. The reaction mixture is stirred at 80° C. for 90 minutes, cooled, and the ethanol formed in the course of the reaction is distilled off at room temperature under a high vacuum. Subsequently, 13.8 g of ground potassium carbonate and a spatula tip of 18-Crown-6 are added and the whole is stirred for 30 minutes at 80° C. 6.7 g of bromoacetic acid methyl ester are then added. The temperature rises to 87° C. After having been stirred for 1 hour at 80° C., the reaction mixture is left at 100° C. for 15 hours. After cooling, undissolved material is removed by filtration and the filtrate is poured into water and extracted with ethyl acetate. The combined extracts are dried, concentrated and purified on silica gel with ethyl acetate/hexane (1:1).

6.4 g (56%) of the title compound of the formula

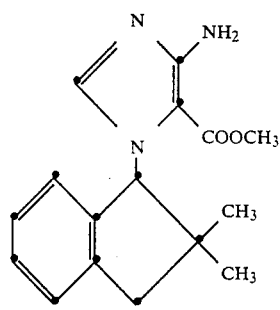

are isolated in the form of crystals having a melting point of 167°–168° C. (Comp. No. 3.02).

Example 3.06:
(+)-4-amino-1-(2,2-dimethyl-1,2,3,4-tetrahydronaphthalen-1-yl)-imidazole-5-carboxylic acid methyl ester 10.5 g (0.06 mol) of (−)-1-amino-2,2-dimethyl-1,2,3,4-tetrahydronaphthalene are dissolved in 50 ml of N,N-dimethylformamide and 5.9 g (0.06 mol) of ethoxymethylenecyanamide are added thereto. The temperature rises to 35° C. The solution is stirred for 2 hours at 80° C., cooled and the ethanol that has formed is distilled off at room temperature under a high vacuum. Subsequently, 20.7 g (0.15 mol) of pulverised potassium carbonate are added and, after stirring has been carried out for 30 minutes at 80° C., 10.1 g (0.066 mol) of bromoacetic acid methyl ester are added to this suspension. The temperature rises to 100° C.

After stirring has been carried out for 15 hours at 100° C., the cooled suspension is poured onto 500 ml of water and extracted with ethyl acetate. The combined organic phases are dried over Na$_2$SO$_4$ and filtered. After the solvent has been distilled off, 15.8 g of a brown oil (crude product) are obtained which are purified on a pressure column (silica gel) with ethyl acetate/hexane 1:1. The resulting 5.3 g of oil are dissolved in 20 ml of ethanol at elevated temperature, treated with active carbon and filtered. The product begins to crystallise out on cooling.

4.1 g (22.9%) of the title compound of the formula

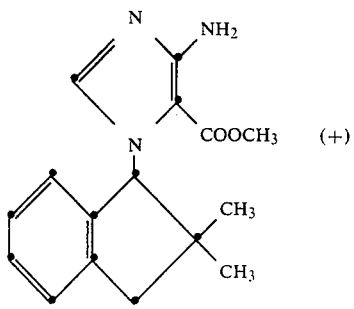

are obtained in the form of a brownish yellow resin with an optical rotation $[\alpha]_D^{20}$ of 54.18 (CHCl$_3$) (Comp. No. 3.143).

Example 3.07:
(−)-4-amino-1-(2,2-dimethylindan-1-yl)-imidazole-5-carboxylic acid methyl ester Analogously to Example 3.01, 26.1 g (88%) of the title compound of the formula

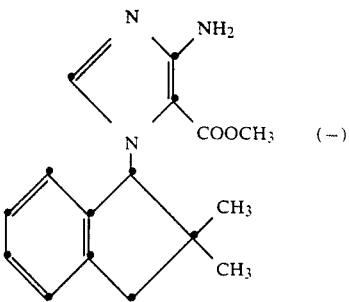

are obtained in the form of crystals having a melting point of 100°–105° C. and an optical rotation $[\alpha]_D^{20}$ of −106.6±0.4° (CHCl$_3$) (Comp. No. 3.144) from 29.7 g of (+)-N-(2,2-dimethylindan-1-yl)-N-(methoxycarbonylmethyl)-aminomethylenecyanamide and 3.8 g of sodium methoxide (30% in methanol) in 100 ml of methanol.

The compounds of Table 3 can be obtained analogously to the above Examples 3.01 to 3.07.

TABLE 3

Compounds of the formula

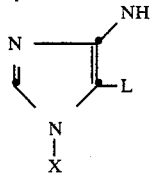

| Comp. No. | X | L | phys. data |
|---|---|---|---|
| 3.01 | 2,2-Dimethyl-1,2,3,4-tetra-hydronaphthalen-1-yl | COOCH$_3$ | M.p. 193–195° C. |
| 3.02 | 2,2-Dimethyl-indan-1-yl | COOCH$_3$ | M.p. 167–168° C. |
| 3.03 | 2,6-Dimethylphenyl | COOCH$_3$ | M.p. 154–156° C. |
| 3.04 | Diphenylmethyl | COOCH$_3$ | M.p. 199–201° C. |
| 3.05 | Indan-1-yl | COOCH$_3$ | |
| 3.06 | 2-Methyl-indan-1-yl | COOCH$_3$ | |
| 3.07 | cis-2-Methyl-indan-1-yl | COOCH$_3$ | |
| 3.08 | trans-2-Methyl-indan-yl | COOCH$_3$ | |
| 3.09 | 1,2,3,4-Tetrahydronaphtha-len-1-yl | COOCH$_3$ | |
| 3.10 | 2-Methyl-1,2,3,4-tetrahydro-naphthalen-1-yl | COOCH$_3$ | |
| 3.11 | cis-2-Methyl-1,2,3,4-tetra-hydronaphthalen-1-yl | COOCH$_3$ | |
| 3.12 | trans-2-Methyl-1,2,3,4-tetrahydro-naphthalen-1-yl | COOCH$_3$ | |
| 3.13 | Benzocycloheptan-5-yl | COOCH$_3$ | |
| 3.14 | 4,5,6,7-Tetrahydrobenzo[b]-thiophen-4-yl | COOCH$_3$ | |
| 3.15 | 4,5,6,7-Tetrahydrobenzo[b]-furan-4-yl | COOCH$_3$ | |
| 3.16 | 5,6,7,8-Tetrahydroquinolin-5-yl | COOCH$_3$ | |
| 3.17 | 5,6,7,8-Tetrahydroiso-quinolin-5-yl | COOCH$_3$ | |
| 3.18 | 5,6,7,8-Tetrahydroquinolin-8-yl | COOCH$_3$ | |
| 3.19 | 5,6,7,8-Tetrahydroiso-quinolin-8-yl | COOCH$_3$ | |
| 3.20 | 9,10-Dihydroanthracen-9-yl | COOCH$_3$ | |
| 3.21 | 9H-Fluoren-9-yl | COOCH$_3$ | |
| 3.22 | Dibenzo[a,d]cyclohepten-5-yl | COOCH$_3$ | |
| 3.23 | Dibenzo[a,d]cycloheptan-5-yl | COOCH$_3$ | |
| 3.24 | 1,2-Dihydronaphthalen-1-yl | COOCH$_3$ | |
| 3.25 | (4-Chlorophenyl)-(phenyl)-methyl | COOCH$_3$ | |
| 3.26 | 2-Ethyl-6-methyl-phenyl | COOCH$_3$ | M.p. 123–127° C. |
| 3.27 | 2,6-Diethyl-phenyl | COOCH$_3$ | M.p. 103–105° C. |
| 3.28 | 2,6-Di-isopropyl-phenyl | COOCH$_3$ | M.p. 127–129° C. |
| 3.29 | 2,4,6-Trimethyl-phenyl | COOCH$_3$ | |
| 3.30 | 4-Chlor-2,6-dimethyl-phenyl | COOCH$_3$ | |
| 3.31 | 2-Ethyl-indan-1-yl | COOCH$_3$ | |
| 3.32 | cis-2-Ethyl-indan-1-yl | COOCH$_3$ | |
| 3.33 | trans-2-Ethyl-indan-1-yl | COOCH$_3$ | |
| 3.34 | 2-Propyl-indan-1-yl | COOCH$_3$ | |
| 3.35 | cis-Propyl-indan-1-yl | COOCH$_3$ | |
| 3.36 | trans-Propyl-indan-1-yl | COOCH$_3$ | |
| 3.37 | 2-Isopropyl-indan-1-yl | COOCH$_3$ | |
| 3.38 | 2-Ethyl-2-methyl-indan-1-yl | COOCH$_3$ | |
| 3.39 | 2-Methyl-2-propyl-indan-1-yl | COOCH$_3$ | |
| 3.40 | 2,2-Diethyl-indan-1-yl | COOCH$_3$ | |
| 3.41 | 2,2-Dipropyl-indan-1-yl | COOCH$_3$ | |
| 3.42 | Spiro-[cyclopropane-1,2'-indan]-1'-yl | COOCH$_3$ | |
| 3.43 | Spiro-[cyclopentane-1,2'-indan]-1'-yl | COOCH$_3$ | |
| 3.44 | Spiro-[cyclohexane1,2'-indan]-1'-yl | COOCH$_3$ | |
| 3.45 | 2-Ethyl-1,2,3,4-tetrahydro-naphthalen-1-yl | COOCH$_3$ | |
| 3.46 | cis-2-Ethyl-1,2,3,4-tetra-hydronaphthalen-1-yl | COOCH$_3$ | |
| 3.47 | trans-2-Ethyl-1,2,3,4-tetra-hydronaphthalen-1-yl | COOCH$_3$ | |
| 3.48 | 2-Propyl-1,2,3,4-tetra-hydronaphthalen-1-yl | COOCH$_3$ | |
| 3.49 | cis-2-Propyl-1,2,3,4-tetra-hydronaphthalen-1-yl | COOCH$_3$ | |
| 3.50 | trans-Propyl-1,2,3,4- | COOCH$_3$ | |

TABLE 3-continued

Compounds of the formula $$\begin{array}{c} NH_2 \\ N \diagdown \diagup \\ \| \quad \| -L \\ N \\ | \\ X \end{array}$$

| Comp. No. | X | L | phys. data |
|---|---|---|---|
| | tetrahydronaphthalen-1-yl | | |
| 3.51 | 2-Ethyl-2-methyl-1,2,3,4-tetrahydronaphthalen-1-yl | COOCH$_3$ | |
| 3.52 | 2-Methyl-2-propyl-1,2,3,4-tetrahydronaphthalen-1-yl | COOCH$_3$ | |
| 3.53 | 2,2-Diethyl-1,2,3,4-tetrahydronaphthalen-1-yl | COOCH$_3$ | |
| 3.54 | 2,2-Dipropyl-1,2,3,4-tetrahydronaphthalen-1-yl | COOCH$_3$ | |
| 3.55 | Spiro[cyclopropan-1,2'-(1',2',3',4'-tetrahydronaphthalen)]-1'-yl | COOCH$_3$ | |
| 3.56 | Spiro[cyclopentan-1,2'-(1',2',3',4'-tetrahydronaphthalen)]-1'-yl | COOCH$_3$ | |
| 3.57 | Spiro[cyclohexan-1,2'-(1',2',3',4'-tetrahydronaphthalen)]-1'-yl | COOCH$_3$ | |
| 3.58 | Chroman-4-yl | COOCH$_3$ | |
| 3.59 | 3-Methylchroman-4-yl | COOCH$_3$ | |
| 3.60 | cis-3-Methylchroman-4-yl | COOCH$_3$ | |
| 3.61 | trans-3-Methylchroman-4-yl | COOCH$_3$ | |
| 3.62 | 3-Ethylchroman-4-yl | COOCH$_3$ | |
| 3.63 | cis-3-Ethylchroman-4-yl | COOCH$_3$ | |
| 3.64 | trans-3-Ethylchroman-4-yl | COOCH$_3$ | |
| 3.65 | 3-Propylchroman-4-yl | COOCH$_3$ | |
| 3.66 | cis-3-Propylchroman-4-yl | COOCH$_3$ | |
| 3.67 | trans-3-Propylchroman-4-yl | COOCH$_3$ | |
| 3,68 | 3-Ethyl-3-methyl-chroman-4-yl | COOCH$_3$ | |
| 3.69 | 3-Methyl-3-propyl-hroman-4-yl | COOCH$_3$ | |
| 3.70 | 3-Isopropylchroman-4-yl | COOCH$_3$ | |
| 3.71 | cis 3-Isopropylchroman-4-yl | COOCH$_3$ | |
| 3.72 | trans-3-Isopropylchroman-4-yl | COOCH$_3$ | |
| 3.73 | 3,3-Dimethylchroman-4-yl | COOCH$_3$ | |
| 3.74 | 3,3-Diethylchroman-4-yl | COOCH$_3$ | |
| 3.75 | 3,3-Dipropylchroman-4-yl | COOCH$_3$ | |
| 3.76 | Spiro[cyclopropane-1,3'-chroman]-4'-yl | COOCH$_3$ | |
| 3.77 | Spiro[cyclopentane-1,3'-chroman]-4'-yl | COOCH$_3$ | |
| 3.78 | Spiro[cyclohexane-1,3'-chroman]-4'-yl | COOCH$_3$ | |
| 3.79 | 2,2-Dimethylindan-1-yl | COOC$_2$H$_5$ | |
| 3.80 | 2,2-Dimethylindan-1-yl | COO-i-C$_3$H$_7$ | |
| 3.81 | 2,2-Dimethylindan-1-yl | COO—CH$_2$—CH=CH$_2$ | |
| 3.82 | 2,2-Dimethylindan-1-yl | COO—(cyclopropyl) | |
| 3.83 | 2,2-Dimethylindan-1-yl | CO—NH CH$_3$ | |
| 3.84 | 2,2-Dimethylindan-1-yl | CO—N(CH$_3$)$_2$ | |
| 3.85 | 2,2-Dimethylindan-1-yl | CN | |
| 3.86 | 2,2-Dimethyl-1,2,3,4-tetrahydronaphthalen-1-yl | COOC$_2$H$_5$ | |
| 3.87 | 2,2-Dimethyl-1,2,3,4-tetrahydronaphthalen-1-yl | COO-i-C$_3$H$_7$ | |
| 3.88 | 2,2-Dimethyl-1,2,3,4-tetrahydronaphthalen-1-yl | COO—CH$_2$—CH=CH$_2$ | |

TABLE 3-continued

Compounds of the formula

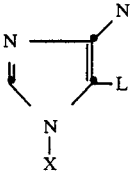

| Comp. No. | X | L | phys. data |
|---|---|---|---|
| 3.89 | 2,2-Dimethyl-1,2,3,4-tetra-hydronaphthalen-1-yl | COO—◁ | |
| 3.90 | 2,2-Dimethyl-1,2,3,4-tetra-hydronaphthalen-1-yl | CO—NH CH$_3$ | |
| 3.91 | 2,2-Dimethyl-1,2,3,4-tetra-hydronaphthalen-1-yl | CO—N(CH$_3$)$_2$ | |
| 3.92 | 2,2-Dimethyl-1,2,3,4-tetra-hydronaphthalen-1-yl | CN | |
| 3.93 | 2,6-Dimethylphenyl | COOC$_2$H$_5$ | |
| 3.94 | 2,6-Dimethylphenyl | COO-i-C$_3$H$_7$ | |
| 3.95 | 2,6-Dimethylphenyl | COO—CH$_2$—CH=CH$_2$ | |
| 3.96 | 2,6-Dimethylphenyl | COO—◁ | |
| 3.97 | 2,6-Dimethylphenyl | CO—NH CH$_3$ | |
| 3.98 | 2,6-Dimethylphenyl | CO—N(CH$_3$)$_2$ | |
| 3.99 | 2,6-Dimethylphenyl | CN | |
| 3.100 | Diphenylmethyl | COOC$_2$H$_5$ | |
| 3.101 | Diphenylmethyl | COO-i-C$_3$H$_7$ | |
| 3.102 | Diphenylmethyl | COO—CH$_2$—CH=CH$_2$ | |
| 3.103 | Diphenylmethyl | COO—◁ | |
| 3.104 | Diphenylmethyl | CO—NH CH$_3$ | |
| 3.105 | Diphenylmethyl | CO—N(CH$_3$)$_2$ | |
| 3.106 | Diphenylmethyl | CN | |
| 3.107 | 2-Methylchroman-4-yl | COOCH$_3$ | |
| 3.108 | cis-2-Methylchroman-4-yl | COOCH$_3$ | |
| 3.109 | trans-2-Methylchroman-4-yl | COOCH$_3$ | |
| 3.110 | 2-Ethylchroman-4-yl | COOCH$_3$ | |
| 3.111 | cis-2-Ethylchroman-4-yl | COOCH$_3$ | |
| 3.112 | trans-2-Ethylchroman-4-yl | COOCH$_3$ | |
| 3.113 | 2-Propylchroman-4-yl | COOCH$_3$ | |
| 3.114 | cis-2-Propylchroman-4-yl | COOCH$_3$ | |
| 3.115 | trans-2-Propylchroman-4-yl | COOCH$_3$ | |
| 3.116 | 2-Ethyl-2-methyl-chroman-4-yl | COOCH$_3$ | |
| 3.117 | 2-Methyl-2-propyl-chroman-4-yl | COOCH$_3$ | |
| 3.118 | 2-Isopropylchroman-4-yl | COOCH$_3$ | |
| 3.119 | cis 2-Isopropylchroman-4-yl | COOCH$_3$ | |
| 3.120 | trans-2-Isopropylchroman-4-yl | COOCH$_3$ | |
| 3.121 | 2,2-Dimethylchroman-4-yl | COOCH$_3$ | |
| 3.122 | 2,2-Diethylchroman-4-yl | COOCH$_3$ | |
| 3.123 | 2,2-Dipropylchroman4-yl | COOCH$_3$ | |
| 3.124 | Spiro[cyclopropane-1,2'-chroman]-4'-yl | COOCH$_3$ | |
| 3.125 | Spiro[cyclopentane-1,2'-chroman]-4'-yl | COOCH$_3$ | |
| 3.126 | Spiro[yclohexane-1,2'-chroman]-4'-yl | COOCH$_3$ | |
| 3.127 | 2,2-Diemthyl-1,2,3,4-tetra-hydronaphthalen-1-yl | CO—NH-i-C$_3$H$_7$ | |
| 3.128 | Thiochroman-4-yl | COOCH$_3$ | |
| 3.129 | 2,2-Dimethylthiochroman-4-yl | COOCH$_3$ | |
| 3.130 | 3,3-Dimethylthiochroman-4-yl | COOCH$_3$ | |

TABLE 3-continued

Compounds of the formula

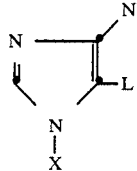

| Comp. No. | X | L | phys. data |
|---|---|---|---|
| 3.131 | 2,3-Dimethylthiochroman-4-yl | COOCH$_3$ | |
| 3.132 | [cis-2,3-Dimethyl]thiochroman-4-yl | COOCH$_3$ | |
| 3.133 | [trans-2,3-Dimethyl]thiochroman-4-yl | COOCH$_3$ | |
| 3.134 | 2-Methylthiochroman-4-yl | COOCH$_3$ | |
| 3.135 | 2-Ethylthiochroman-4-yl | COOCH$_3$ | |
| 3.136 | 2-Methyl-2-ethylthiochroman-4-yl | COOCH$_3$ | |
| 3.137 | 2,2-Diethylthiochroman-4-yl | COOCH$_3$ | |
| 3.138 | 3,3-Diuethylthiochroman-4-yl | COOCH$_3$ | |
| 3.139 | 3-Methyl-3-ethyl-thiochroman-4-yl | COOCH$_3$ | |
| 3.140 | 2,3-Dimethylindan-1-yl | COOCH$_3$ | |
| 3.141 | [cis-2,3-Dimethyl]indan-1-yl | COOCH$_3$ | |
| 3.142 | [trans-2,3-Dimethyl]indan-1-yl | COOCH$_3$ | |
| 3.143 | (+)-2,2-Dimethylindan-1-yl | COOCH$_3$ | $[\alpha]_D^{20}+54.18$ (CHCl$_3$) |
| 3.144 | (−)-2,2-Dimethylindan-1-yl | COOCH$_3$ | M.p. 100–105° C. |
| 3.145 | (+)-2,2-Dimethyl-1,2,3,4-tetrahydronaphthalen-1-yl | COOCH$_3$ | |
| 3.146 | (−)-2,2-Dimethyl-1,2,3,4-tetrahydronaphthalen-1-yl | COOCH$_3$ | |

PREPARATION EXAMPLE 4: DIAZONIUM SALTS OF THE FORMULA VI

Example 4.01:
5-methoxycarbonyl-1-(2,2-dimethyl-1,2,3,4-tetrahydronaphth-1-yl)-imidazole-4-diazonium tetrafluoroborate 8.3 g (0.028 mol) of compound No. 3.01 are dissolved in 100 ml of acetic acid/propionic acid 1:1 and 24.6 g (0.14 mol) of 50% hydrofluoroboric acid/H$_2$O are added dropwise thereto. Then, 4.7 g (0.067 mol) of NaNO$_2$ are introduced at 0° and the whole is stirred at 0° for a further 5 hours, during which time the product is precipitated in the form of crystals. The suspension is left overnight at room temperature, diluted with ice-water, and the product is filtered off with suction and dried over KOH.

8.9 g (97%) of the title compound of the formula

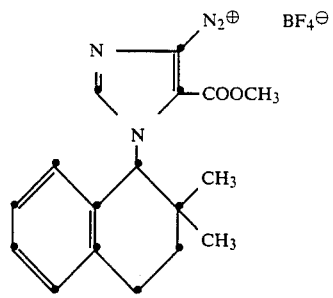

are isolated in the form of colourless crystals having a melting point of 178° C. (decomp.) (Comp. No. 4.01).

Example 4.02:
1-(2,2-dimethyl-indan-1-yl)-5-methoxycarbonylimidazole-4-diazonium hexafluorophosphate Analogously to Example 4.01, the title compound of the formula

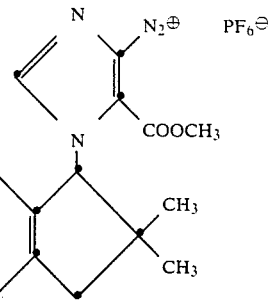

is obtained in the form of crystals having a melting point of 172°–174° C. (decomp.) from 4-amino-1-(2,2-dimethylindan-1-yl)imidazole-5-carboxylic acid methyl ester and hexafluorophosphoric acid.

The salts of Table 4 can be obtained analogoulsy to the above Example.

TABLE 4

Salts of the formula

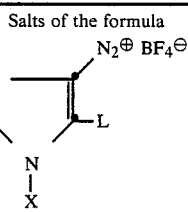

| Comp. No. | X | L | phys. data |
|---|---|---|---|
| 4.01 | 2,2-Dimethyl-1,2,3,4-tetra-hydronaphthalen-1-yl | COOCH$_3$ | M.p. 178° C. (decomp.) |
| 4.02 | 2,2-Dimethyl-indan-1-yl | COOCH$_3$ | M.p. 154–156° C. (decomp.) |
| 4.03 | 2,6-Dimethylphenyl | COOCH$_3$ | |
| 4.04 | Diphenylmethyl | COOCH$_3$ | M.p. 159–161° C. |
| 4.05 | Indan-1-yl | COOCH$_3$ | |
| 4.06 | 2-Methyl-indan-1-yl | COOCH$_3$ | |
| 4.07 | cis-2-Methyl-indan-1-yl | COOCH$_3$ | |
| 4.08 | trans-2-Methyl-indan-1-yl | COOCH$_3$ | |
| 4.09 | 1,2,3,4-Tetrahydronaphtha-len-1-yl | COOCH$_3$ | |
| 4.10 | 2-Methyl-1,2,3,4-tetrahydro-naphthalen-1-yl | COOCH$_3$ | |
| 4.11 | cis-2-Methyl-1,2,3,4-tetra-hydronaphthalen-1-yl | COOCH$_3$ | |
| 4.12 | trans-2-Methyl-1,2,3,4-tetrahydro-naphthalen-1-yl | COOCH$_3$ | |
| 4.13 | Benzocycloheptan-5-yl | COOCH$_3$ | |
| 4.14 | 4,5,6,7-Tetrahydrobenzo[b]-thiophen-4-yl | COOCH$_3$ | |
| 4.15 | 4,5,6,7-Tetrahydrobenzo[b]-furan-4-yl | COOCH$_3$ | |
| 4.16 | 5,6,7,8-Tetrahydroquinolin-5-yl | COOCH$_3$ | |
| 4.17 | 5,6,7,8-Tetrahydroiso-quinolin-5-yl | COOCH$_3$ | |
| 4.18 | 5,6,7,8-Tetrahydroquinolin-8-yl | COOCH$_3$ | |
| 4.19 | 5,6,7,8-Tetrahydroiso-quinolin-8-yl | COOCH$_3$ | |
| 4.20 | 9,10-Dihydroanthracen-9-yl | COOCH$_3$ | |
| 4.21 | 9H-Fluoren-9-yl | COOCH$_3$ | |
| 4.22 | Dibenzo[a,d]cyclohepten-5-yl | COOCH$_3$ | |
| 4.23 | Dibenzo[a,d]cycloheptan-5-yl | COOCH$_3$ | |
| 4.24 | 1,2-Dihydronaphthalen-1-yl | COOCH$_3$ | |
| 4.25 | (4-Chlorophenyl)-(phenyl)-methyl | COOCH$_3$ | |
| 4.26 | 2-Ethyl-6-methyl-phenyl | COOCH$_3$ | |
| 4.27 | 2,6-Diethyl-phenyl | COOCH$_3$ | |
| 4.28 | 2,6-Di-isopropyl-phenyl | COOCH$_3$ | |
| 4.29 | 2,4,6-Trimethyl-phenyl | COOCH$_3$ | |
| 4.30 | 4-Chloro-2,6-dimethyl-phenyl | COOCH$_3$ | |
| 4.31 | 2-Ethyl-indan-1-yl | COOCH$_3$ | |
| 4.32 | cis-2-Ethyl-indan-1-yl | COOCH$_3$ | |
| 4.33 | trans-2-Ethyl-indan-1-yl | COOCH$_3$ | |
| 4.34 | 2-Propyl-indan-1-yl | COOCH$_3$ | |
| 4.35 | cis-Propyl-indan-1-yl | COOCH$_3$ | |
| 4.36 | trans-Propyl-indan-1-yl | COOCH$_3$ | |
| 4.37 | 2-Isopropyl-indan-1-yl | COOCH$_3$ | |
| 4.38 | 2-Ethyl-2-methyl-indan-1-yl | COOCH$_3$ | |
| 4.39 | 2-Methyl-2-propyl-indan-1-yl | COOCH$_3$ | |
| 4.40 | 2,2-Diethyl-indan-1-yl | COOCH$_3$ | |
| 4.41 | 2,2-Dipropyl-indan-1-yl | COOCH$_3$ | |
| 4.42 | Spiro-[cyclopropan-1,2'-indan]-1'-yl | COOCH$_3$ | |
| 4.43 | Spiro-[cyclopentane-1,2'-indan]-1'-yl | COOCH$_3$ | |
| 4.44 | Spiro-[cyclohexane-1,2'-indan]-1'-yl | COOCH$_3$ | |
| 4.45 | 2-Ethyl-1,2,3,4-tetrahydro-naphthalen-1-yl | COOCH$_3$ | |
| 4.46 | cis-2-Ethyl-1,2,3,4-tetra-hydronaphthalen-1-yl | COOCH$_3$ | |
| 4.47 | trans-2-Ethyl-1,2,3,4-tetra-hydronaphthalen-1-yl | COOCH$_3$ | |
| 4.48 | 2-Propyl-1,2,3,4-tetra-hydronaphthalen-1-yl | COOCH$_3$ | |
| 4.49 | cis-2-Propyl-1,2,3,4-tetra- | COOCH$_3$ | |

TABLE 4-continued

Salts of the formula $$\text{structure with } N_2^{\oplus} BF_4^{\ominus}, N, N-X, L$$

| Comp. No. | X | L | phys. data |
|---|---|---|---|
| | hydronaphthalen-1-yl | | |
| 4.50 | trans-2-Propyl-1,2,3,4-tetrahydronaphthalen-1-yl | COOCH$_3$ | |
| 4.51 | 2-Ethyl-2-methyl-1,2,3,4-tetrahydronaphthalen-1-yl | COOCH$_3$ | |
| 4.52 | 2-Methyl-2-propyl-1,2,3,4-tetrahydronaphthalen-1-yl | COOCH$_3$ | |
| 4.53 | 2,2-Diethyl-1,2,3,4-tetrahydronaphthalen-1-yl | COOCH$_3$ | |
| 4.54 | 2,2-Dipropyl-1,2,3,4-tetrahydronaphthalen-1-yl | COOCH$_3$ | |
| 4.55 | Spiro[cyclopropane-1,2'-(1',2',3',4'-tetrahydronaphthalen)]-1'-yl | COOCH$_3$ | |
| 4.56 | Spiro[cyclopentane-1,2'-(1',2',3',4'-tetrahydronaphthalen)]-1'-yl | COOCH$_3$ | |
| 4.57 | Spiro[cyclohexane-1,2'-(1',2',3',4'-tetrahydronaphthalen)]-1'-yl | COOCH$_3$ | |
| 4.58 | Chroman-4-yl | COOCH$_3$ | |
| 4.59 | 3-Methylchroman-4-yl | COOCH$_3$ | |
| 4.60 | cis-3-Methylchroman-4-yl | COOCH$_3$ | |
| 4.61 | trans-3-Methylchroman-4-yl | COOCH$_3$ | |
| 4.62 | 3-Ethylchroman-4-yl | COOCH$_3$ | |
| 4.63 | cis-3-Ethylchroman-4-yl | COOCH$_3$ | |
| 4.64 | trans-3-Ethylchroman-4-yl | COOCH$_3$ | |
| 4.65 | 3-Propylchroman-4-yl | COOCH$_3$ | |
| 4.66 | cis-3-Propylchroman-4-yl COOCH$_3$ | | |
| 4.67 | trans-3-Propylchroman-4-yl | COOCH$_3$ | |
| 4.68 | 3-Ethyl-3-methyl-chroman-4-yl | COOCH$_3$ | |
| 4.69 | 3-Methyl-3-propyl-chroman-4-yl | COOCH$_3$ | |
| 4.70 | 3-Isopropylchroman-4-yl | COOCH$_3$ | |
| 4.71 | cis 3-Isopropylchroman-4-yl | COOCH$_3$ | |
| 4.72 | trans-3-Isopropylchroman-4-yl | COOCH$_3$ | |
| 4.73 | 3,3-Dimethylchroman-4-yl | COOCH$_3$ | |
| 4.74 | 3,3-Diethylchroman-4-yl | COOCH$_3$ | |
| 4.75 | 3,3-Dipropylchroman-4-yl | COOCH$_3$ | |
| 4.76 | Spiro[cyclopropane-1,3'-chroman]-4'-yl | COOCH$_3$ | |
| 4.77 | Spiro[cyclopentane-1,3'-chroman]-4'-yl | COOCH$_3$ | |
| 4.78 | Spiro[cyclohexane-1,3'-chroman]-4'-yl | COOCH$_3$ | |
| 4.79 | 2,2-Dimethylindan-1-yl | COOC$_2$H$_5$ | |
| 4.80 | 2,2-Dimethylindan-1-yl | COO-i-C$_3$H$_7$ | |
| 4.81 | 2,2-Dimethylindan-1-yl | COO—CH$_2$—CH=CH$_2$ | |
| 4.82 | 2,2-Dimethylindan-1-yl | COO—cyclopropyl | |
| 4.83 | 2,2-Dimethylindan-1-yl | CO—NH CH$_3$ | |
| 4.84 | 2,2-Dimethylindan-1-yl | CO—N(CH$_3$)$_2$ | |
| 4.85 | 2,2-Dimethylindan-1-yl | CN | |
| 4.86 | 2,2-Dimethyl-1,2,3,4-tetrahydronaphthalen-1-yl | COOC$_2$H$_5$ | |
| 4.87 | 2,2-Dimethyl-1,2,3,4-tetrahydronaphthalen-1-yl | COO-i-C$_3$H$_7$ | |
| 4.88 | 2,2-Dimethyl-1,2,3,4-tetrahydronaphthalen-1-yl | COO—CH$_2$—CH=CH$_2$ | |

TABLE 4-continued

Salts of the formula

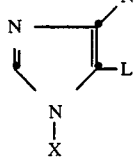

| Comp. No. | X | L | phys. data |
|---|---|---|---|
| 4.89 | 2,2-Dimethyl-1,2,3,4-tetra-hydronaphthalen-1-yl | 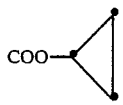 | |
| 4.90 | 2,2-Dimethyl-1,2,3,4-tetra-hydronaphthalen-1-yl | CO—NH CH$_3$ | |
| 4.91 | 2,2-Dimethyl-1,2,3,4-tetra-hydronaphthalen-1-yl | CO—N(CH$_3$)$_2$ | |
| 4.92 | 2,2-Dimethyl-1,2,3,4-tetra-hydronaphthalen-1-yl | CN | |
| 4.93 | 2,6-Dimethylphenyl | COOC$_2$H$_5$ | |
| 4.94 | 2,6-Dimethylphenyl | COO-i-C$_3$H$_7$ | |
| 4.95 | 2,6-Dimethylphenyl | COO—CH$_2$—CH=CH$_2$ | |
| 4.96 | 2,6-Dimethylphenyl | 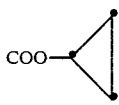 | |
| 4.97 | 2,6-Dimethylphenyl | CO—NH CH$_3$ | |
| 4.98 | 2,6-Dimethylphenyl | CO—N(CH$_3$)$_2$ | |
| 4.99 | 2,6-Dimethylphenyl | CN | |
| 4.100 | Diphenylmethyl | COOC$_2$H$_5$ | |
| 4.101 | Diphenylmethyl | COO-i-C$_3$H$_7$ | |
| 4.102 | Diphenylmethyl | COO—CH$_2$—CH=CH$_2$ | |
| 4.103 | Diphenylmethyl | 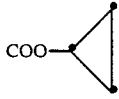 | |
| 4.104 | Diphenylmethyl | CO—NH CH$_3$ | |
| 4.105 | Diphenylmethyl | CO—N(CH$_3$)$_2$ | |
| 4.106 | Diphenylmethyl | CN | |
| 4.107 | 2-Methylchroman-4-yl | COOCH$_3$ | |
| 4.108 | cis-2-Methylchroman-4-yl | COOCH$_3$ | |
| 4.109 | trans-2-Methylchroman-4-yl | COOCH$_3$ | |
| 4.110 | 2-Ethylchroman-4-yl | COOCH$_3$ | |
| 4.111 | cis-2-Ethylchroman-4-yl | COOCH$_3$ | |
| 4.112 | trans-2-Ethylchroman-4-yl | COOCH$_3$ | |
| 4.113 | 2-Propylchroman-4-yl | COOCH$_3$ | |
| 4.114 | cis-2-Propylchroman-4-yl | COOCH$_3$ | |
| 4.115 | trans-2-Propylchroman-4-yl | COOCH$_3$ | |
| 4.116 | 2-Ethyl-2-methyl-chroman-4-yl | COOCH$_3$ | |
| 4.117 | 2-Methyl-2-propyl-chroman-4-yl | COOCH$_3$ | |
| 4.118 | 2-Isopropylchroman-4-yl | COOCH$_3$ | |
| 4.119 | cis 2-Isopropylchroman-4-yl | COOCH$_3$ | |
| 4.120 | trans-2-Isopropylchroman-4-yl | COOCH$_3$ | |
| 4.121 | 2,2-Dimethylchroman-4-yl | COOCH$_3$ | |
| 4.122 | 2,2-Diethylchroman-4-yl | COOCH$_3$ | |
| 4.123 | 2,2-Dipropylchroman-4-yl | COOCH$_3$ | |
| 4.124 | Spiro[cyclopropane-1,2'-chroman]-4°-yl | COOCH$_3$ | |
| 4.125 | Spiro[cyclopentane-1,2'-chroman]-4'-yl | COOCH$_3$ | |
| 4.126 | Sprio[cyclohexane-1,2'-chroman]-4'-yl | COOCH$_3$ | |
| 4.127 | 2,2-Dimethyl-1,2,3,4-tetra-hydronaphthalen-1-yl | CO—NH-i-C$_3$H$_7$ | |
| 4.128 | Thiochroman-4-yl | COOCH$_3$ | |
| 4.129 | 2,2-Dimethylthiochroman-4-yl | COOCH$_3$ | |
| 4.130 | 3,3-Dimethylthiochroman-4-yl | COOCH$_3$ | |

TABLE 4-continued

Salts of the formula $$\text{structure with } N_2^{\oplus} BF_4^{\ominus}$$

| Comp. No. | X | L | phys. data |
|---|---|---|---|
| 4.131 | 2,3-Dimethylthiochroman-4-yl | COOCH$_3$ | |
| 4.132 | [cis-2,3-Dimethyl]thiochroman-4-yl | COOCH$_3$ | |
| 4.133 | [trans-2,3-Dimethyl]thiochroman-4-yl | COOCH$_3$ | |
| 4.134 | 2-Methylthiochroman-4-yl | COOCH$_3$ | |
| 4.135 | 2-Ethylthiochroman-4-yl | COOCH$_3$ | |
| 4.136 | 2-Methyl-2-ethyl-thiochroman-4-yl | COOCH$_3$ | |
| 4.137 | 2,2-Diethylthiochroman-4-yl | COOCH$_3$ | |
| 4.138 | 3,3-Diethylthiochroman-4-yl | COOCH$_3$ | |
| 4.139 | 3-Methyl-3-ethyl-thiochroman-4-yl | COOCH$_3$ | |
| 4.140 | 2,3-Dimethylindan-1-yl | COOCH$_3$ | |
| 4.141 | [cis-2,3-Dimethyl]indan-1-yl | COOCH$_3$ | |
| 4.142 | [trans-2,3-Dimethyl]indan-1-yl | COOCH$_3$ | |
| 4.143 | (+)-2,2-Dimethylindan-1-yl | COOCH$_3$ | |
| 4.144 | (−)-2,2-Dimethylindan-1-yl | COOCH$_3$ | |
| 4.145 | (+)-2,2-Dimethyl-1,2,3,4-tetrahydronaphthalen-1-yl | COOCH$_3$ | |
| 4.146 | (−)-2,2-Dimethyl-1,2,3,4-tetrahydronaphthalen-1-yl | COOCH$_3$ | |

PREPARATION EXAMPLE 5: IMIDAZOLES OF THE FORMULA I

Example 5.01:
1-(2,2-dimethyl-1,2,3,4-tetrahydronaphthalen-1-yl)-imidazole-5-carboxylic acid methyl ester 6.0 g (0.02 mol) of compound 3.01 are dissolved in 30 ml of acetic acid/propionic acid 1:1, and 11.5 g (0.1 mol) of 85% phosphoric acid are added dropwise thereto. The solution is cooled to 0° and, at that temperature, 1.4 g (0.02 mol) of NaNO$_2$ are introduced, the whole is maintained at 0° for 6 hours and then 13.2 g (0.1 mol) of 50% H$_3$PO$_2$/H$_2$O are added dropwise thereto. The resulting yellow suspension is maintained at 0° for 15 hours, during which time a clear yellowish red solution is formed. The solution is added to 1 l of ice-water, adjusted to pH 7 with NaOH and extracted by shaking with ethyl acetate. The organic phase is dried over Na$_2$SO$_4$/carbon and the solvent is distilled off. The red oil that remains is chromatographed on silica gel with ethyl acetate/hexane 1:2.

3.3 g (59%) of the title compound of the formula

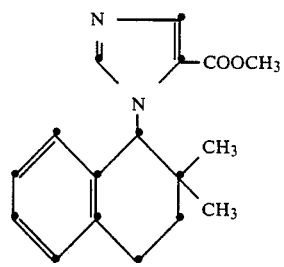

are isolated in the form of colourless crystals having a melting point of 101°–104° C. (Comp. No. 5.01).

Example 5.02:
1-diphenylmethyl-imidazole-5-carboxylic acid methyl ester 2.0 g (6.5 mmol) of compound 3.04 are dissolved in 20 ml of acetic acid/propionic acid 1:1 and 4.9 g (19.5 mmol) of 50% HBF$_4$/H$_2$O are added thereto. Subsequently, 0.9 g (6.5 mmol) of 50% NaNO$_2$/H$_2$O are added dropwise at 0° C. The orange-red solution is maintained at 0° after 3 hours and then 4.3 g (32.5 mmol) of 50% of H$_3$PO$_2$/H$_2$O are added dropwise thereto. The solution is then maintained at 0° for 48 hours, subsequently added to ice/water, adjusted to pH 7 with NaOH and extracted by shaking with ethyl acetate. The organic phase is dried over Na$_2$SO$_4$/carbon, the solvent is distilled off, and the residue is chromatographed on silica gel with ethyl acetate/hexane 1:2.

1.8 g (48%) of the title compound of the formula

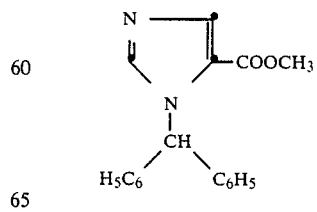

are isolated in the form of colourless crystals having a melting point of 126°–129° C. (Comp. No. 5.04).

Example 5.03: Process for the preparation of compounds of the formula I from amines of the formula VIII without isolation of the intermediates: 1-(2,2-dimethylindan-1-yl)-imidazole-5-carboxylic acid methyl ester 3.9 g of ethoxymethylenecyanamide are added to a solution of 6.4 g of 1-amino-2,2-dimethylindane in 50 ml of dimethylformamide. The temperature rises to 40° C. The reaction mixture is stirred for 1½ hours at 80° C., cooled and the ethanol that has formed is filtered off with suction at room temperature under a high vacuum.

13.8 g of ground potassium carbonate and a spatula tip of 18-Crown-6 are then added, the whole is stirred at 80° C. for 30 minutes, and then 6.7 g of bromoacetic acid methyl ester are added. The temperature rises to 87° C. After stirring has been carried out for 1 hour at 80° C., the reaction mixture is maintained at 100° C. for 15 hours. After cooling to room temperature, the salts are filtered off and subsequently washed with 10 ml of DMF. This solution is added dropwise, within 30 minutes, to a solution of 6.8 g of tert.-butyl nitrite in 30 ml of dimethylformamide at 60°–62° C. and this temperature is maintained for 1 hour until no more nitrogen is evolved. The solution is poured onto ice and extracted with ethyl acetate. The combined extracts are washed with brine, dried over sodium sulphate, rendered colourless with active carbon, filtered over Hyflo and concentrated by evaporation. The residue is purified on silica gel (150 g) using ethyl acetate/hexane 1:1. In this manner 7 g of a yellow oil are obtained from which a crystalline product is obtained by trituration with hexane.

5.2 g of the title compound of the formula

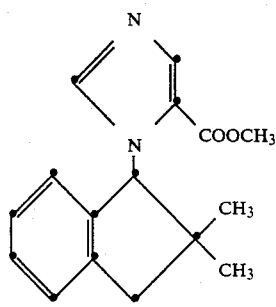
(Comp. No. 5.2)

are obtained in the form of crystals having a melting point of 100°–102° C.

Example 5.04:
(+)-1-(2,2-dimethyl-1,2,3,4-tetrahydronaphthalen-1-yl)-imidazole-5-carboxylic acid methyl ester 1.7 g (0.015 mol) of 90% tert.-butyl nitrite are dissolved in 20 ml of N,N-dimethylformamide. A solution of 2.6 g (0.0087 mol) of (+)-4-amino-1-(2,2-dimethyl-1,2,3,4-tetrahydronaphthalen-1-yl)-imidazole-5-carboxylic acid methyl ester in 20 ml of N,N-dimethylformamide is added dropwise thereto at 60°–62° C. within a period of 30 minutes and that temperature is maintained for a further 70 minutes until no further nitrogen is evolved. The cooled solution is poured onto ice and extracted with ethyl acetate. The ethyl acetate phase is washed with brine, dried over $Na_2SO_4$ and filtered. Removal of the solvent by distillation yields 2.4 g of a brown oil (crude product), which is purified on a pressure column (silica gel) with ethyl acetate/hexane 1:1.

1.5 g (60%) of the title compound of the formula

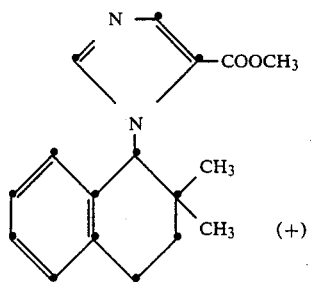

are isolated in the form of crystals having a melting point of 66°–67.5° C. and an optical rotation $[\alpha]_D^{20}$ of 64.8° (Comp. No. 5.145).

Example 5.05:
(−)-1-(2,2-dimethylindan-1-yl)-imidazole-5-carboxylic acid methyl ester From two separate dropping funnels, a solution of 11.0 g of (−)-4-amino-1-(2,2-dimethylindan-1-yl)-imidazole-5-carboxylic acid methyl ester in 17.2 g of 50% hypophosphorous acid and 40 ml of dimethylformamide, and a solution of 2.7 g of sodium nitrite in 10 ml of water, are simultaneously added dropwise to 4.4 g of phosphoric acid (85%) in 100 ml of water. The whole is then stirred at 0° C. for 2 hours, poured into water and adjusted to pH 7 with 30% sodium hydroxide solution. The aqueous phase is extracted with ethyl acetate. After drying, concentrating and purifying the organic phase on silica gel with ethyl acetate/hexane, 10.5 g of a brown oil are obtained which crystallises on drying under a high vacuum.

7.1 g of the title compound of the formula

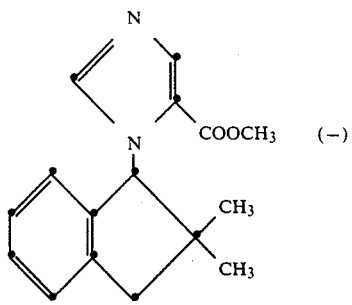

are isolated in the form of pink crystals having a melting point of 74°–76° C. and an optical rotation $[\alpha]_D^{20}$ of −66.5±0.4° C. ($CHCl_3$) (Comp. No. 5.144).

The compounds of Table 5 can be obtained analogously to the above Examples 5.01 to 5.05.

TABLE 5

Compounds of the formula

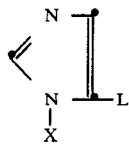

| Comp. No. | X | L | phys. data |
|---|---|---|---|
| 5.01 | 2,2-Dimethyl-1,2,3,4-tetrahydronaphthalen-1-yl | COOCH$_3$ | M.p. 101–104° C. |
| 5.02 | 2,2-Dimethyl-indan-1-yl | COOCH$_3$ | M.p. 100–102° C. |
| 5.03 | 2,6-Dimethylphenyl | COOCH$_3$ | M.p. 88–91° C. |
| 5.04 | Diphenylmethyl | COOCH$_3$ | M.p. 126–129° C. |
| 5.05 | Indan-1-yl | COOCH$_3$ | M.p. 140° C.[1] |
| 5.06 | 2-Methyl-indan-1-yl | COOCH$_3$ | M.p. 137–138° C.[1] |
| 5.07 | cis-2-Methyl-indan-1-yl | COOCH$_3$ | resin |
| 5.08 | trans-2-Methyl-indan-1-yl | COOCH$_3$ | resin |
| 5.09 | 1,2,3,4-Tetrahydronaphtalin-1-yl | COOCH$_3$ | M.p. 63° C. |
| 5.10 | 2-Methyl-1,2,3,4-tetrahydronaphthalen-1-yl | COOCH$_3$ | M.p. 90–92° C. |
| 5.11 | cis-2-Methyl-1,2,3,4-tetrahydronaphthalen-1-yl | COOCH$_3$ | M.p. 101–102° C. |
| 5.12 | trans-2-Methyl-1,2,3,4-tetrahydro-naphthalen-1-yl | COOCH$_3$ | M.p. 110–110.5° C. |
| 5.13 | Benzocycloheptan-5-yl | COOCH$_3$ | |
| 5.14 | 4,5,6,7-Tetrahydrobenzo[b]-thiophen-4-yl | COOCH$_3$ | M.p. 223.5° C.[2] |
| 5.15 | 4,5,6,7-Tetrahydrobenzo[b]-furan-4-yl | COOCH$_3$ | |
| 5.16 | 5,6,7,8-Tetrahydroquinolin-5-yl | COOCH$_3$ | |
| 5.17 | 5,6,7,8-Tetrahydroisoquinolin-5-yl | COOCH$_3$ | |
| 5.18 | 5,6,7,8-Tetrahydroquinolin-8-yl | COOCH$_3$ | |
| 5.19 | 5,6,7,8-Tetrahydroisoquinolin-8-yl | COOCH$_3$ | |
| 5.20 | 9,10-Dihydroanthracen-9-yl | COOCH$_3$ | |
| 5.21 | 9H-Fluoren-9-yl | COOCH$_3$ | M.p. 146° C. |
| 5.22 | Dibenzo[a,d]cyclohepten-5-yl | COOCH$_3$ | |
| 5.23 | Dibenzo[a,d]cycloheptan-5-yl | COOCH$_3$ | |
| 5.24 | 1,2-Dihydronaphthalen-1-yl | COOCH$_3$ | |
| 5.25 | (4-Chlorophenyl)-(phenyl)-methyl | COOCH$_3$ | |
| 5.26 | 2-Ethyl-6-methyl-phenyl | COOCH$_3$ | oil |
| 5.27 | 2,6-Diethyl-phenyl | COOCH$_3$ | |
| 5.28 | 2,6-Di-isopropyl-phenyl | COOCH$_3$ | |
| 5.29 | 2,4,6-Trimethyl-phenyl | COOCH$_3$ | |
| 5.30 | 4-Chloro-2,6-dimethyl-phenyl | COOCH$_3$ | |
| 5.31 | 2-Ethyl-indan-1-yl | COOCH$_3$ | |
| 5.32 | cis-2-Ethyl-indan-1-yl | COOCH$_3$ | |
| 5.33 | trans-2-Ethyl-indan-1-yl | COOCH$_3$ | |
| 5.34 | 2-Propyl-indan-1-yl | COOCH$_3$ | |
| 5.35 | cis-Propyl-indan-1-yl | COOCH$_3$ | |
| 5.36 | trans-Propyl-indan-1-yl | COOCH$_3$ | |
| 5.37 | 2-Isopropyl-indan-1-yl | COOCH$_3$ | |
| 5.38 | 2-Ethyl-2-methyl-indan-1-yl | COOCH$_3$ | resin |
| 5.39 | 2-Methyl-2-propyl-indan-1-yl | COOCH$_3$ | |
| 5.40 | 2,2-Diethyl-indan-1-yl | COOCH$_3$ | M.p. 83.5–85° C. |
| 5.41 | 2,2-Dipropyl-indan-1-yl | COOCH$_3$ | |
| 5.42 | Spiro-[cyclopropane-1,2'-indan]-1'-yl | COOCH$_3$ | |
| 5.43 | Spiro-[cyclopentane-1,2'-indan]-1'-yl | COOCH$_3$ | resin |
| 5.44 | Spiro-[cyclohexane-1,2'-indan]-1'-yl | COOCH$_3$ | |
| 5.45 | 2-Ethyl-1,2,3,4-tetrahydronaphthalen-1-yl | COOCH$_3$ | |
| 5.46 | cis-2-Ethyl-1,2,3,4-tetrahydronaphthalen-1-yl | COOCH$_3$ | |
| 5.47 | trans-2-Ethyl-1,2,3,4-tetrahydronaphthalen-1-yl | COOCH$_3$ | |
| 5.48 | 2-Propyl-1,2,3,4-tetrahydronaphthalen-1-yl | COOCH$_3$ | resin |
| 5.49 | cis-2-Propyl-1,2,3,4-tetrahydronaphthalen-1-yl | COOCH$_3$ | |
| 5.50 | trans-2-Propyl-1,2,3,4-tetrahydronaphthalen-1-yl | COOCH$_3$ | |

TABLE 5-continued

Compounds of the formula

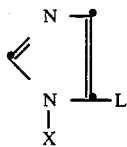

| Comp. No. | X | L | phys. data |
|---|---|---|---|
| 5.51 | 2-Ethyl-2-methyl-1,2,3,4-tetrahydronaphthalen-1-yl | COOCH$_3$ | |
| 5.52 | 2-Methyl-2-propyl-1,2,3,4-tetrahydronaphthalen-1-yl | COOCH$_3$ | |
| 5.53 | 2,2-Diethyl-1,2,3,4-tetrahydronaphthalen-1-yl | COOCH$_3$ | M.p. 109–110° C. |
| 5.54 | 2,2-Dipropyl-1,2,3,4-tetrahydronaphthalen-1-yl | COOCH$_3$ | |
| 5.55 | Spiro[cyclopropane-1,2'-(1',2',3',4'-tetrahydronaphthalen)]-1'-yl | COOCH$_3$ | |
| 5.56 | Spiro[cyclopentane-1,2'-(1',2',3',4'-tetrahydronaphthalen)]-1'-yl | COOCH$_3$ | M.p. 153–154° C. |
| 5.57 | Spiro[cyclohexane-1,2'-(1',2',3',4'-tetrahydronaphthalen)]-1'-yl | COOCH$_3$ | M.p. 177–178° C. |
| 5.58 | Chroman-4-yl | COOCH$_3$ | |
| 5.59 | 3-Methylchroman-4-yl | COOCH$_3$ | |
| 5.60 | cis-3-Methylchroman-4-yl | COOCH$_3$ | |
| 5.61 | trans-3-Methylchroman-4-yl | COOCH$_3$ | |
| 5.62 | 3-Ethylchroman-4-yl | COOCH$_3$ | |
| 5.63 | cis-3-Ethylchroman-4-yl | COOCH$_3$ | |
| 5.64 | trans-3-Ethylchroman-4-yl | COOCH$_3$ | |
| 5.65 | 3-Propylchroman-4-yl | COOCH$_3$ | |
| 5.66 | cis-3-Propylchroman-4-yl | COOCH$_3$ | |
| 5.67 | trans-3-Propylchroman-4-yl | COOCH$_3$ | |
| 5.68 | 3-Ethyl-3-methyl-chroman-4-yl | COOCH$_3$ | |
| 5.69 | 3-Methyl-3-propyl-chroman-4-yl | COOCH$_3$ | |
| 5.70 | 3-Isopropylchroman-4-yl | COOCH$_3$ | |
| 5.71 | cis 3-Isopropylchroman-4-yl | COOCH$_3$ | |
| 5.72 | trans-3-Isopropylchroman-4-yl | COOCH$_3$ | |
| 5.73 | 3,3-Dimethylchroman-4-yl | COOCH$_3$ | |
| 5.74 | 3,3-Diethylchroman-4-yl | COOCH$_3$ | |
| 5.75 | 3,3-Dipropylchroman-4-yl | COOCH$_3$ | |
| 5.76 | Spiro[cyclopropane-1,3'-chroman]-4'-yl | COOCH$_3$ | |
| 5.77 | Spiro[cyclopentane-1,3'-chroman]-4'-yl | COOCH$_3$ | |
| 5.78 | Spiro[cyclohexane-1,3'-chroman]-4'-yl | COOCH$_3$ | |
| 5.79 | 2,2-Dimethylindan-1-yl | COOC$_2$H$_5$ | M.p. 124–125° C. |
| 5.80 | 2,2-Dimethylindan-1-yl | COO-i-C$_3$H$_7$ | M.p. 140–141° C. |
| 5.81 | 2,2-Dimethylindan-1-yl | COO—CH$_2$—CH=H$_2$ | |
| 5.82 | 2,2-Dimethylindan-1-yl | COO—⊿ | |
| 5.83 | 2,2-Dimethylindan-1-yl | CO—NH CH$_3$ | |
| 5.84 | 2,2-Dimethylindan-1-yl | CO—N(CH$_3$)$_2$ | |
| 5.85 | 2,2-Dimethylindan-1-yl | CN | |
| 5.86 | 2,2-Dimethyl-1,2,3,4-tetrahydronaphthalen-1-yl | COOC$_2$H$_5$ | M.p. 74–75° C. |
| 5.87 | 2,2-Dimethyl-1,2,3,4-tetrahydronaphthalen-1-yl | COO-i-C$_3$H$_7$ | |
| 5.88 | 2,2-Dimethyl-1,2,3,4-tetrahydronaphthalen-1-yl | COO—CH$_2$—CH=CH$_2$ | |
| 5.89 | 2,2-Dimethyl-1,2,3,4-tetrahydronaphthalen-1-yl | COO—⊿ | |

TABLE 5-continued

Compounds of the formula

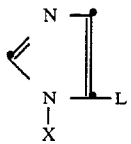

| Comp. No. | X | L | phys. data |
|---|---|---|---|
| 5.90 | 2,2-Dimethyl-1,2,3,4-tetra-hydronaphthalen-1-yl | CO—NH CH$_3$ | |
| 5.91 | 2,2-Dimethyl-1,2,3,4-tetra-hydronaphthalen-1-yl | CO—N(CH$_3$)$_2$ | |
| 5.92 | 2,2-Dimethyl-1,2,3,4-tetra-hydronaphthalen-1-yl | CN | |
| 5.93 | 2,6-Dimethylphenyl | COOC$_2$H$_5$ | |
| 5.94 | 2,6-Dimethylphenyl | COO-i-C$_3$H$_7$ | |
| 5.95 | 2,6-Dimethylphenyl | COO—CH$_2$—CH=CH$_2$ | |
| 5.96 | 2,6-Dimethylphenyl | COO—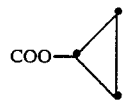 | |
| 5.97 | 2,6-Dimethylphenyl | CO—NH CH$_3$ | |
| 5.98 | 2,6-Dimethylphenyl | CO—N(CH$_3$)$_2$ | |
| 5.99 | 2,6-Dimethylphenyl | CN | |
| 5.100 | Diphenylmethyl | COOC$_2$H$_5$ | |
| 5.101 | Diphenylmethyl | COO-i-C$_3$H$_7$ | |
| 5.102 | Diphenylmethyl | COO—CH$_2$—CH=CH$_2$ | |
| 5.103 | Diphenylmethyl | COO—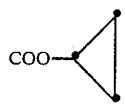 | |
| 5.104 | Diphenylmethyl | CO—NH CH$_3$ | |
| 5.105 | Diphenylmethyl | CO—N(CH$_3$)$_2$ | |
| 5.106 | Diphenylmethyl | CN | |
| 5.107 | 2-Methylchroman-4-yl | COOCH$_3$ | |
| 5.108 | cis-2-Methylchroman-4-yl | COOCH$_3$ | |
| 5.109 | trans-2-Methylchroman-4-yl | COOCH$_3$ | |
| 5.110 | 2-Ethylchroman-4-yl | COOCH$_3$ | |
| 5.111 | cis-2-Ethylchroman-4-yl | COOCH$_3$ | |
| 5.112 | trans-2-Ethylchroman-4-yl | COOCH$_3$ | |
| 5.113 | 2-Propylchroman-4-yl | COOCH$_3$ | |
| 5.114 | cis-2-Propylchroman-4-yl | COOCH$_3$ | |
| 5.115 | trans-2-Propylchroman-4-yl | COOCH$_3$ | |
| 5.116 | 2-Ethyl-2-methyl-chroman-4-yl | COOCH$_3$ | |
| 5.117 | 2-Methyl-2-propyl-chroman-4-yl | COOCH$_3$ | |
| 5.118 | 2-Isopropylchroman-4-yl | COOCH$_3$ | |
| 5.119 | cis 2-Isopropylchroman-4-yl | COOCH$_3$ | |
| 5.120 | trans-2-Isopropylchroman-4-yl | COOCH$_3$ | |
| 5.121 | 2,2-Dimethylchroman-4-yl | COOCH$_3$ | |
| 5.122 | 2,2-Diethylchroman-4-yl | COOCH$_3$ | |
| 5.123 | 2,2-Dipropylchroman-4-yl | COOCH$_3$ | |
| 5.124 | Spiro[cyclopropane-1,2'-chroman]-4'-yl | COOCH$_3$ | |
| 5.125 | Spiro[cyclopentane-1,2'-chroman]-4'-yl | COOCH$_3$ | |
| 5.126 | Spiro[cyclohexane-1,2'-chroman]-4'-yl | COOCH$_3$ | |
| 5.127 | 2,2-Dimethyl-1,2,3,4-tetra-hydronaphthalen-1-yl | CO—NH-i-C$_3$H$_7$ | |
| 5.128 | Thiochroman-4-yl | COOCH$_3$ | |
| 5.129 | 2,2-Dimethylthiochroman-4-yl | COOCH$_3$ | |
| 5.130 | 3,3-Dimethylthiochroman-4-yl | COOCH$_3$ | |
| 5.131 | 2,3-Dimethylthiochroman-4-yl | COOCH$_3$ | |
| 5.132 | [cis-2,3-Dimethyl]thio-chroman-4-yl | COOCH$_3$ | |
| 5.133 | [trans-2,3-Dimethyl]thio-chroman-4-yl | COOCH$_3$ | |
| 5.134 | 2-Methylthiochroman-4-yl | COOCH$_3$ | |
| 5.135 | 2-Ethylthiochroman-4-yl | COOCH$_3$ | |

TABLE 5-continued

Compounds of the formula

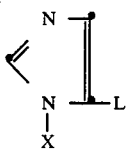

| Comp. No. | X | L | phys. data |
|---|---|---|---|
| 5.136 | 2-Methyl-2-ethyl-thio-chroman-4-yl | COOCH$_3$ | |
| 5.137 | 2,2-Diethyl-thiochroman-4-yl | COOCH$_3$ | |
| 5.138 | 3,3-Diethyl-thiochroman-4-yl | COOCH$_3$ | |
| 5.139 | 3-Methyl-3-ethyl-thio-chroman-4-yl | COOCH$_3$ | |
| 5.140 | 2,3-Dimethylindan-1-yl | COOCH$_3$ | |
| 5.141 | [cis-2,3-Dimethyl]indan-1-yl | COOCH$_3$ | |
| 5.142 | [trans-2,3-Dimethyl]indan-1-yl | COOCH$_3$ | |
| 5.143 | (+)-2,2-Dimethylindan-1-yl | COOCH$_3$ | |
| 5.144 | (−)-2,2-Dimethylindan-1-yl | COOCH$_3$ | M.p. 74–76° C. |
| 5.145 | (+)-2,2-Dimethyl-1,2,3,4-tetrahydronaphthalen-1-yl | COOCH$_3$ | M.p. 66–67.5° C. |
| 5.146 | (−)-2,2-Dimethyl-1,2,3,4-tetrahydronaphthalen-1-yl | COOCH$_3$ | |

[1] The compound is characterised as an NHO$_3$ salt (1)
[2] The compound is characterised as an HCl salt (1:1)

I claim:
1. A process for the preparation of imidazoles of the formula I

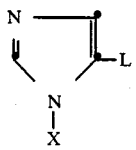

in which

L and X represent L$^1$ and X$^1$; L$^2$ and X$^2$; L$^3$ and X$^3$; or L$^4$ and X$^4$; respectively, and L$^1$ represents COOR$^1$; CONR$^2$R$^3$; CONR$^4$NHR$^3$; or CN;

R$^1$ represents hydrogen; C$_1$–C$_7$-alkyl; C$_3$–C$_7$-alkenyl; C$_3$–C$_7$-alkynyl; C$_3$–C$_7$-cycloalkyl; C$_1$–C$_7$-alkoxy-C$_1$–C$_7$-alkyl; or aryl-C$_1$–C$_5$-alkyl; the radicals R$^2$, R$^3$ and R$^4$, independently of one another, each represents hydrogen; C$_1$–C$_5$-alkyl; C$_3$–C$_5$-alkenyl; C$_3$–C$_5$-alkynyl; C$_3$–C$_7$-cycloalkyl; aryl; or C$_1$–C$_5$-alkyl substituted by aryl, C$_3$–C$_7$-cycloalkyl, C$_3$–C$_7$-cycloalkoxy, C$_1$–C$_5$-alkoxy, hydroxy, carboxy or by C$_1$–C$_5$-alkoxycarbonyl; or R$^2$ and R$^3$, together with the nitrogen atom to which they are bonded, represent a piperidinyl, pyrrolidinyl, 2-oxopiperidinyl, 2-oxopyrrolidinyl, morpholinyl, thiomorpholinyl, piperazinyl or 4-(C$_1$–C$_4$)-alkyl-piperazinyl ring that is unsubstituted or is substituted by from 1 to 3 C$_1$–C$_5$-alkyl groups;

X$^1$ represents 1-indanyl, 1-tetrahydronaphthalenyl, 5-benzocycloheptanyl, 4-tetrahydrobenzothienyl, 4-tetrahydrobenzofuranyl, 5-tetrahydroquinolinyl, 5-tetrahydroisoquinolinyl, 8-tetrahydroquinolinyl, 8-tetrahydroisoquinolinyl, 9,10-dihydro-9-anthracenyl, 9H-fluoren-9-yl, 5-dibenzo(a,d)cycloheptenyl, 5-dibenzo(a,d)cycloheptanyl or 1-dihydornaphthalenyl, each of which is unsubstituted or is substituted up to six times by the same or different substituents selected from C$_1$–C$_5$-alkyl, aryl-C$_1$–C$_5$-alkyl, diaryl-C$_1$–C$_5$-alkyl, C$_1$–C$_5$-alkoxy, halogen, C$_3$–C$_7$-alkenyl, amino, nitro, C$_1$–C$_5$-alkylcarbonylamino, trifluoromethyl and difluoromethoxy, or in which two geminally bonded substituents, together with the carbon atom to which they are bonded, form a C$_3$–C$_7$-spirocycloalkyl group, or in which two substituents together represent a C$_1$–C$_5$-alkylene or C$_5$–C$_7$-cycloalkylene group, it being possible for this alkylene or cycloalkylene group in turn optionally to be substituted up to twice by the same or different substituents selected from C$_1$–C$_5$-alkyl, aryl-C$_1$–C$_5$-alkyl, diaryl-C$_1$–C$_5$-alkyl, C$_1$–C$_5$-alkoxy, halogen, C$_3$–C$_7$-alkenyl, trifluoromethyl, difluoromethoxy and aryl; or X$^1$ represents the group

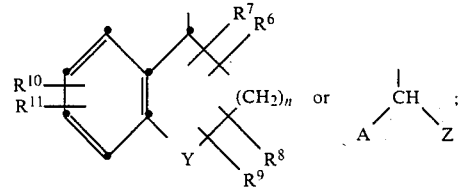

n represents 0; 1; or 2;

Y represents a group —CH$_2$S(O)$_m$— or —CH$_2$—N(R$^{1-2}$)— in which the hetero atom is bonded to the benzene ring carbon atom and in which m represents 0, 1 or 2;

R$^6$, R$^7$, R$^8$ and R$^9$, independently of one another, each represents hydrogen; C$_1$–C$_5$-alkyl; aryl-C$_1$–C$_5$-alkyl; diaryl-C$_1$–C$_5$-alkyl; C$_1$–C$_5$-alkoxy; halogen; C$_3$–C$_7$-alkenyl; trifluoromethyl; difluoromethoxy; or aryl; or R$^6$ and R$^7$ together represent a fused benzene radical which can optionally be substituted up to twice by C$_1$–C$_5$-alkyl, C$_1$–C$_5$-alkoxy, halogen, mono- to tri-halo-substituted C$_1$–C$_5$-alkyl, mono- to tri-halo-substituted C$_1$–C$_5$-alkoxy, nitro, amino or by —NH—CO—M; or $R^6$ and $R^7$, together with the carbon atom to which they are geminally bonded, represent a spirocyclic $C_3$-$C_7$-ring; or $R^6$ and $R^7$ together represent a $C_1$-$C_5$-alkylene or $C_5$-$C_7$-cycloalkylene group which can optionally be substituted up to twice by the same or different substituents selected from $C_1$-$C_5$-alkyl, aryl-$C_1$-$C_5$-alkyl, $C_1$-$C_5$-alkoxy, halogen, $C_3$-$C_7$-alkenyl, trifluoromethyl, difluoromethoxy and aryl; and $R^{10}$ and $R^{11}$, independently of one another, each represents hydrogen; $C_1$-$C_5$-alkyl; $C_1$-$C_5$-alkoxy; halogen; trifluoromethyl; difluoromethoxy; cyano; nitro; amino; mono-$C_1$-$C_5$-alkylamino; di-$C_1$-$C_5$-alkylamino; or —NH—CO—M; and $R^{12}$ represent hydrogen; $C_1$-$C_5$-alkyl; $C_1$-$C_5$-alkanoyl; or 4-methylphenylsulphonyl; and A represents hydrogen; $C_3$-$C_7$-cycloalkyl optionally substituted up to twice by $C_1$-$C_5$-alkyl; $C_1$-$C_7$-alkyl optionally substituted by $C_1$-$C_7$-alkoxy or by aryl; $C_1$-$C_7$-alkyl substituted by a $C_1$-$C_7$-alkoxy and by an aryl radical; or pyridinyl, pyrimidinyl, naphthalenyl, furanyl or thiophenyl, each of which is unsubstituted or is substituted up to twice by the same or different substituents selected from $C_1$-$C_5$-alkyl, $C_1$-$C_5$-alkoxy, halogen, nitro, amino, mono-$C_1$-$C_5$-alkylamino, di-$C_1$-$C_5$-alkylamino, —NH—CO—M, cyano, trifluoromethyl and difluoromethoxy;

and within the scope of the definition of A, aryl represents phenyl, pyridinyl, pyrimidinyl, naphthalenyl, furanyl or thiophenyl, and this radical can be substituted up to twice, or in the case when aryl is phenyl up to three times, by the same or different substituents selected from $C_1$-$C_5$-alkyl, $C_1$-$C_5$-alkoxy, halogen nitro, amino, mono-$C_1$-$C_5$-alkyl amino, di-$C_1$-$C_5$-alkylamino, —NH—CO—M, cyano, trifluoromethyl and difluoromethoxy; and Z represents naphthalenyl, thiophenyl, furanyl, pyrimidinyl, phenyl or pyridinyl, each of which is unsubstituted or is substituted up to three times by the same or different substituents selected from $C_1$-$C_5$-alkyl, $C_1$-$C_5$-alkoxy, halogen, cyano, nitro, amino, mono-$C_1$-$C_5$-alkylamino, di-$C_1$-$C_5$-alkylamino, —NH—CO—M, trifluoromethyl and difluoromethoxy; and M represents $C_1$-$C_5$-alkyl; and aryl within the scope of the above definitions of the radicals X and L may also represent a phenyl radical that is unsubstituted or is substituted up to three times by the same or different substituents selected from $C_1$-$C_5$-alkyl, $C_1$-$C_5$-alkoxy and halogen; and $L^2$ represents CO—D—$R^{13}$;

D represents O; or $NR^{13}$;

$R^{13}$ represents hydrogen; phenyl; $C_3$-$C_6$-alkenyl; or $C_1$-$C_{12}$-alkyl that is unsubstituted or is substituted up to three times by the same or different substituents selected from $C_1$-$C_6$-alkoxy, $C_1$-$C_3$-dialkylamino and halogen; and $R^{13}$, when D is O, additionally represents a cation of a metal of group I, II or VII of the Periodic Table or of ammonium; and $X^2$ represents a radical

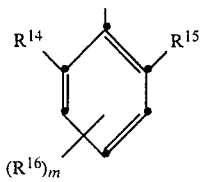

m represents 0, 1, 2 or 3; and $R^{14}$ and $R^{15}$, independently of one another, each represents $C_1$-$C_4$-alkyl;

$R^{16}$ represents the same or different radicals selected from the group comprising $C_1$-$C_4$-alkyl, $C_1$-$C_4$-alkoxy and halogen;

$L^3$ represents CN; $COOR^{17}$; or $CONR^{18}R^{19}$; and $R^{17}$ represents unsubstituted or halo-substituted $C_1$-$C_7$-alkyl, $C_3$-$C_7$-alkenyl, $C_3$-$C_7$-alkynyl, $C_1$-$C_7$-alkoxy-$C_1$-$C_7$-alkyl, $C_3$-$C_7$-cycloalkyl or aryl-$C_1$-$C_5$-alkyl; and $R^{18}$ and $R^{19}$, which may be the same or different, represent hydrogen; $C_1$-$C_4$-alkyl; $C_3$-$C_7$-alkenyl; $C_3$-$C_7$-alkynyl; or $C_1$-$C_7$-alkoxy-$C_1$-$C_7$-alkyl; or $R^{18}$ and $R^{19}$, together with the nitrogen atom to which they are bonded, represent a saturated or unsaturated three- to seven-membered ring that contains up to three hetero atoms selected from the group comprising O, N and S and that is unsubstituted or is substituted by $(C_1$-$C_4)$-alkyl or by halogen and may contain a carbonyl group; and $X^3$ represents a radical

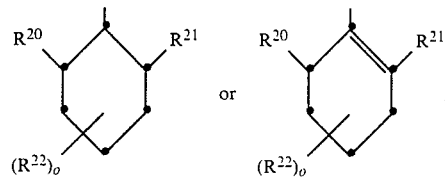

o represents from 0 to 6;

$R^{20}$ and $R^{21}$, independently of one another, each represents hydrogen or $C_1$-$C_4$-alkyl; and $R^{22}$ represents, independently of any other, $C_1$-$C_4$-alkyl; $C_1$-$C_4$alkoxy; $C_1$-$C_4$-hydroxyalkyl; $C_1$-$C_4$-alkoxy-$C_1$-$C_4$-alkyl; or halogen; and $L^4$ represents CO—$R^{23}$; or CN;

$R^{23}$ represents hydroxy; $C_1$-$C_6$-alkoxy; hydroxy-$(C_2$-$C_6)$-alkoxy; $(C_2$-$C_6)$-alkoxyalkoxy; amino; $C_1$-$C_6$-alkylamino; di-$(C_1$-$C_6)$-alkylamino; di-$(C_1$-$C_6)$-alkylamino-$(C_1$-$C_3)$-alkylamino; $C_1$-$C_3$-alkoxyamino; anilino; N-pyrrolidino; N-piperidino; N-morpholino; hydrazino; $N'$-$(C_1$-$C_3)$-alkylhydrazino; N,N'-dimethylhydrazino; or N'-phenylhydrazino; and $X^4$ represents the radical

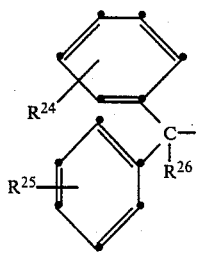

and $R^{24}$ and $R^{25}$, which may be the same or different, represent hydrogen; halogen; $C_1$–$C_3$-alkyl; trifluoromethyl; hydroxy; $C_1$–$C_3$-alkoxy; halo-($C_1$–$C_3$)-alkoxy; $C_1$–$C_3$-alkylthio; cyano; nitro; or acetamido; and $R^{26}$ represents hydrogen; or phenyl;

wherein an N-cyanoformamidine of the formula II $$X-NH-CH=N-CN \qquad (II),$$

in which X has the definition given above, is N-alkylated with a compound of the formula III $$Z-CH_2-L \qquad (III),$$

in which L has the definition given above and Z represents a nucleofugal group, to form a compound of the formula IV

and IV is cyclised under the action of bases to form a 4-aminoimidazole of the formula V

and the aminoimidazole V is reduced to form an imidazole of the formula I.

2. A process according to claim 1 for the preparation of imidazoles of the formula I
in which
L represents $COOR^1$; $CONR^2R^3$; or CN; and
$R^1$ represents hydrogen; $C_1$–$C_7$-alkyl; $C_3$–$C_7$-alkenyl; $C_3$–$C_7$-alkynyl; $C_3$–$C_7$-cycloalkyl; $C_1$–$C_7$-alkoxy-$C_1$–$C_7$-alkyl; or aryl-$C_1$–$C_5$-alkyl; the radicals $R^2$, $R^3$ and $R^4$, independently of one another, each represents hydrogen; $C_1$–$C_5$-alkyl; $C_3$–$C_5$-alkenyl; $C_3$–$C_5$-alkynyl; $C_3$–$C_7$-cycloalkyl; aryl; or $C_1$–$C_5$-alkyl substituted by aryl, $C_3$–$C_7$-cycloalkyl, $C_3$–$C_7$-cycloalkoxy, $C_1$–$C_5$-alkoxy, hydroxy, carboxy or by $C_1$–$C_5$-alkoxycarbonyl; or $R^2$ and $R^3$, together wit the nitrogen atom to which they are bonded, represent a piperidinyl, pyrrolidinyl, 2-oxopiperidinyl, 2-oxopyrrolidinyl, morpholinyl, thiomorpholinyl, piperazinyl or 4-($C_1$–$C_4$)-alkyl-piperazinyl ring that is unsubstituted or is substituted by from 1 to 3 $C_1$–$C_5$-alkyl groups; and X represents 1,2,3,4-tetrahydronaphthalen-1-yl, indan-1-yl, phenyl, diphenylmethyl, benzocycloheptan-5-yl, 4,5,6,7-tetrahydrobenzo(b)-thiophen-4-yl, 4,5,6,7-tetrahydrobenzo(b)furan-4-yl, 5,6,7,8-tetrahydroquinolin-5-yl, 5,6,7,8-tetrahydroisoquinolin-5-yl, 5,6,7,8-tetrahydroquinolin-8-yl, 5,6,7,8-tetrahydroisoquinolin-8-yl, 9,10-dihydroanthracen-9-yl, 9H-fluoren-9-yl, dibenzo(a,d)cyclohepten-5-yl, dibenzo(a,d)cycloheptan-5-yl, 1,2-dihydronaphthalen-1-yl, chroman-4-yl or thiochroman-4-yl, each of which is unsubstituted or is substituted up to three times by $C_1$–$C_4$-alkyl or by halogen, or in which two geminally bonded substituents, together with the carbon atom to which they are bonded, form a $C_3$–$C_6$-spiroalkyl group.

3. A process according to claim 1 for the preparation of imidazoles of the formula I
in which
L represents $COOR^1$; CN; or $CNR^2R^3$; and
$R^1$ represents $C_1$–$C_4$-alkyl; $C_3$–$C_6$-alkenyl; or $C_3$–$C_6$-cyclo-alkyl;
$R^2$ and $R^3$, independently of one another, each represents hydrogen or $C_1$–$C_4$-alkyl; and
X represents 2,2-dimethyl-1,2,3,4-tetrahydronaphthalen-1-yl, 2,2-dimethylindan-1-yl, 2,6-dimethylphenyl, diphenylmethyl, indan-1-yl, 2-methylindan-1-yl, cis-2-methylindan-1-yl, trans-2-methylindan-1-yl, 1,2,3,4-tetrahydronaphthalen-1-yl, 2-methyl-1,2,3,4-tetrahydronaphthalen-1-yl, cis-2-methyl-1,2,3,4-tetrahydronaphthalen-1-yl, trans-2-methyl-1,2,3,4-tetrahydronaphthalen-1-yl, benzocycloheptan-5yl, 4,5,6,7-tetrahydrobenzo(b)thiophen-4-yl, 4,5,6,7-tetrahydrobenzo(b)furan-4-yl, 5,6,7,8-tetrahydroquinolin-5-yl, 5,6,7,8-tetrahydroisoquinolin-5-yl, 5,6,7,8-tetrahydroquinolin-8-yl, 5,6,7,8-tetrahydroisoquinolin-8-yl, 9,10-dihydroanthracen-9-yl, 9H-fluoren-9-yl, dibenzo(a,d)cyclohepten-5-yl, dibenzo(a,d,)cycloheptan-5-yl, 1,2-dihydronaphthalen-1-yl, (4-chlorophenyl)-(phenyl)-methyl, 2-ethyl-6-methylphenyl, 2,6-diethylphenyl, 2,6-diisopropylphenyl, 2,4,6-trimethylphenyl, 4-chloro-2,6-dimethylphenyl, 2-ethylindan-1-yl, cis-2-ethylindan-1-yl, trans-2-ethylindan-1-yl, 2-propylindan-1-yl, cis-propylindan-1-yl, trans-propylindan-1-yl, 2-isopropylindan-1-yl, 2-ethyl-2-methylindan-1-yl, 2-methyl-2-propylindan-1-yl, 2,2-diethylindan-1-yl, 2,2-dipropylindan-1-yl, spiro(cyclopropane-1,2'-indan)-1'-yl, spiro(cyclopentane-1,2'-indan)-1'-yl, spiro(cyclohexane-1,2'-indan)-1'-yl, 2-ethyl-1,2,3,4-tetrahydronaphthalen-1-yl, cis-2-ethyl-1,2,3,4-tetrahydronaphthalen-1-yl, trans-2-ethyl-1,2,3,4-tetrahydronaphthalen-1-yl, 2-propyl-1,2,3,4-tetrahydronapthalen-1-yl, cis-2-propyl-1,2,3,4-tetrahydronaphthalen-1-yl, trans-2-propyl-1,2,3,4-tetrahydronaphthalen-1-yl, 2-ethyl-2-methyl-1,2,3,4-tetrahydronaphthalen-1-yl, 2-methyl-2-propyl-1,2,3,4-tetrahydronaphthalen-1-yl, 2,2-diethyl-1,2,3,4-tetrahydronaphthalen-1-yl, 2,2-dipropyl-1,2,3,4-tetrahydronaphthalen-1-yl, spiro(cyclopropane-1,2'-(1',2',3',4'-tetrahydronaphthalen))-1'-yl, sprio(cyclopentane-1,2'-(1',2',3',4'-tetrahydronaphthalen))-1'-yl, spiro(cyclohexane-1,2'-(1',2',3',4'-tetrahydronaphthalen))-1'-yl, chroman-4-yl, 3-methylchroman-4-yl, cis-3-methylchroman-4-yl, trans-3-methylchroman-4-yl, 3-ethylchroman-4-yl, cis-3-ethylchroman-4-yl, trans-3-ethylchroman-4-yl, 3-propylchroman-4-yl, cis-3-propylchroman-4-yl, trans-3-propylchroman-4-yl, 3-ethyl-3-methylchroman-4-yl, 3-methyl-3-propylchroman-4-yl, 3-isopropylchroman-4-yl, cis-3-isopropylchroman-4-yl, trans-3-isopropylchroman-4yl, 3,3-dimethylchroman-4-yl, 3,3-diethylchroman-4-yl, 3,3-dipropylchroman-4-yl, spiro(cyclopropane-1,3'-chroman)-4'-yl, spiro(cyclopentane-1,3'-chroman)-4'-yl, spiro(cyclohexane-1,3'-chroman)-4'-yl, 2-methylchroman-4-yl, cis-2-methylchroman-4-yl, trans-2-methylchroman-4-yl, 2-ethylchroman-4-yl, cis-2-ethylchroman-4-yl, trans-2-ethylchroman-4-yl, 2-propylchroman-4-yl, cis-2-propylchroman-4-yl, trans-2-propylchroman-4-yl, 2-ethyl-2-methylchroman-4-yl, 2-methyl-2-propylchroman-4-yl, 2-isopropylchroman-4-yl, cis-2-isopropylchroman-4-yl, trans-2-isopropylchroman-4-yl, 2,2-dimethylchroman-4-yl, 2,2-diethylchroman-4-yl, 2,2-dipropylchroman-4-yl, spiro(cyclopropane-1,2'-chroman)-4'-yl, spiro(cyclopentane-1,2'-chroman)-4'-yl, spiro(cyclohexane-1,2'-chroman)-4'-yl, 2,2-dimethyl-1,2,3,4-tetrahydronaphthalen-1-yl, thiochroman-4-yl, 2,2-dimethylthiochroman-4-yl, 3,3-dimethylthiochroman-4-yl, 2,3-dimethylthiochroman-4-yl, (cis-2,3-dimethyl)thiochroman-4-yl, (trans-2,3-dimethyl)thiochroman-4-yl, 2-methylthiochroman-4-yl, 2-ethylthiochroman-4-yl, 2-methyl-2-ethylthiochroman-4-yl, 2,2-diethylthiochroman-4-yl, 3,3-diethylthiochroman-4-yl, 3-methyl-3-ethylthio chroman-4-yl, 2,3-dimethylindan-1-yl, (cis-2,3-dimethyl)indan-1-yl, (trans-2,3-dimethyl)indan-1-yl, (+)-2,2-dimethylindan-1-yl, (−)-2,2-dimethylindan-1-yl, (+)-2,2-dimethyl-1,2,3,4-tetrahydronaphthalen-1-yl, (−)-2,2-dimethyl-1,2,3,4-tetrahydronaphthalen-1-yl.

* * * * *